United States Patent [19]

Tsien et al.

[11] Patent Number: 4,603,209
[45] Date of Patent: Jul. 29, 1986

[54] FLUORESCENT INDICATOR DYES FOR CALCIUM IONS

[75] Inventors: Roger Y. Tsien, Berkeley, Calif.; Grzegorz Grynkiewicz, Warsaw, Poland

[73] Assignee: The Regents of the University of California, Berkeley, Calif.

[21] Appl. No.: 648,649

[22] Filed: Sep. 7, 1984

[51] Int. Cl.$^4$ ............... C07C 101/447; C07D 307/87; C07D 209/14

[52] U.S. Cl. .................................. 548/236; 436/800; 546/171; 548/469; 560/44; 549/444; 549/451; 562/426; 562/436; 562/452

[58] Field of Search ...................... 8/648; 427/64, 152; 436/800; 546/81, 171, 89, 64, 70, 153, 158, 49, 56; 549/451, 444; 548/490, 471, 418, 215, 236; 260/465 D, 465 E; 562/426, 431, 452

[56] References Cited

PUBLICATIONS

Arthur H. Schmidt, "Bromotrimethylsilane—Versatile Reagents for Organic Synthesis", Aldrichimica Acta., vol. 14, No. 2, 1981.

Roger Y. Tsien "Intracellular Measurements of Ion Activities" Ann. Rev. Biophys. Bioeng., 1983, 12:91–116.

Roger Y. Tsien, "New Calcium Indicators and Buffers with High Selectivity Against Magnesium and Protons: Design, Synthesis, and Properties of Prototype", Am. Chem. Soc., 1980.

*Primary Examiner*—Veronica P. Hoke
*Attorney, Agent, or Firm*—Fitch, Even, Tabin & Flannery

[57] ABSTRACT

The present invention discloses a new class of highly fluorescent indicator dyes that are specific for calcium ions. The new fluorescent indicator dyes combine a stilbene-type fluorophore with a tetracarboxylate parent $Ca^{2+}$ chelating compound having the octacoordinate pattern of liganding groups characteristic of EGTA and BAPTA. Preferred forms contain extra heterocyclic bridges to reinforce the ethylenic bond of the stilbene and to reduce hydrophobicity. Compared to their widely used predecessor, "quin2", the new dyes offer up to thirty-fold brighter fluorescence, major changes in wavelength (not just intensity) upon $Ca^{2+}$ binding, slightly lower affinities for $Ca^{2+}$, slightly longer wavelengths of excitation, and considerably improved selectivity for $Ca^{2+}$ over other divalent cations. These properties, particularly the wavelength sensitivity to $Ca^{2+}$, make the dyes useful indicators for many intracellular applications, especially in single cells, adherent cell layers, or bulk tissues.

The present invention also discloses an improved method for synthesizing alpha-acyloxyalkyl bromides wherein the bromides so synthesized are free of contaminating bis(1-bromoalkyl)ether. The improved method is exemplified herein in the synthesis of acetoxymethyl bromide, a compound useful in preparing the acetoxymethyl esters disclosed herein as novel $Ca^{2+}$ specific fluorescent indicators.

30 Claims, 7 Drawing Figures

FLUORESCENT INDICATOR DYES FOR CALCIUM IONS

ACKNOWLEDGMENT

This invention was made with government support under Grant NAGW-515 awarded by NASA and Grants No.: GM-31004 and EY-04372 awarded by the National Institutes of Health. The government has certain rights in this invention.

FIELD OF THE INVENTION

The present invention relates to fluorescent indicator dyes that are specific for calcium ions. More specifically, the present invention relates to fluorescent, calcium-specific indicator dyes that fluoresce at different wavelengths depending on whether dye has bound calcium or is free of calcium. This wavelength shift makes it possible to measure calcium concentrations on an absolute scale by simply determining the ratio of fluorescence at the two wavelengths.

In addition the present invention relates to an improved method for synthesizing alpha-acyloxyalkyl bromides, especially acetoxymethyl bromide which is useful in preparing the acetoxymethyl esters contained within the class of new fluorescent dyes disclosed herein.

BACKGROUND OF THE INVENTION

Because of the importance of calcium as an intracellular messenger and regulator, a wide variety of techniques have been developed for measuring intracellular free calcium concentrations $[Ca^{2+}]_i$ (see reference 4). The most successful of these techniques uses dyes or proteins which change absorption or luminescence upon binding $Ca^{2+}$ ions. Currently the most popular of these methods is to monitor the fluorescence of a BAPTA (1,2-bis(2-aminophenoxy)ethane-N,N,N',N'-tetracetic acid) like indicator dye compound called "quin2" (see references 4-7). When this method is used to measure intracellular free calcium in mammalian cells, quin2 is loaded into intact cells by incubating them with a membrane-permeant ester derivative. Cytosolic esterases then split off the ester groups, leaving the membrane-impermeant quin2 tetra-anion trapped in the cytosol. The fluorescence of quin2 provides a measure of cytosolic free calcium concentrations. It is calibrated by interpolation between the limiting fluorescence levels obtained by forcing the trapped dye to known saturatingly high as well as vanishingly low levels of calcium.

Although quin2 has revealed much important biological information, it has severe and acknowledged limitations (see references 5 and 7). For example, quin2's preferred excitation wavelength of 339 nm is too short since it falls within the ultraviolet range. UV irradiation excites significant autofluorescence from the cells being monitored. In addition, such UV irradiation could cause biological side effects in the cells being tested. Also, it is known that light in this UV range does not penetrate microscope optics very well.

A second problem with quin2 is the fact that its extinction coefficient ($<5000$) and fluorescence quantum yield (0.03 to 0.14), though comparable to dansyl groups in aqueous solution, are too low. These spectroscopic properties mean that quin2 loadings of several tenths of millimolar or more are necessary to overcome cell autofluorescence. In some cell types, this much loading significantly buffers $[Ca^{2+}]_i$ transients.

A third problem with quin2 is the fact that it signals $Ca^{2+}$ by increasing its fluorescence intensity without much shift in either excitation or emission wavelengths. Unfortunately, fluorescence intensity is also dependent on other poorly quantified or variable factors such as illumination intensity, emission collection efficiency, dye concentration, and effective cell thickness in the optical beam. As a result, it would be better to have an indicator dye that responded to calcium by shifting wavelengths while still maintaining strong fluorescence. The ratio of the fluorescences of two suitably chosen wavelengths would then signal calcium while cancelling out most or all of the possible variability due to instrument efficiency and content of effective dye.

A fourth problem with quin2 is that it does not measure calcium at micromolar levels. The high effective affinity of quin2 for $Ca^{2+}$ is ideal for measuring levels near or below typical resting values of $[Ca^{2+}]_i$, i.e., near $10^{-7}$M. Unfortunately, at micro levels of calcium or above, quin2 approaches saturation so that further changes in fluorescence intensity are small. As a result, dyes with weaker affinities are needed to quantify calcium at these elevated levels.

Finally, the selectivity of quin2 for calcium over magnesium and heavy metal divalent cations could bear improvement. Quin2 binds $Mg^{2+}$ with a dissociation constant of 1-2 mM. Though $Mg^{2+}$ has little effect on the fluorescence of quin2 when excited at 339 nm, variations in $[Mg^{2+}]_i$ would affect the effective affinity for $Ca^{2+}$ and the calibration scale for the fluorescence signals. Also, cells with unusually high levels of exchangeable heavy metals can give falsely low readings of $[Ca^{2+}]_i$ because the heavy metals quench quin2 fluorescence (see reference 8). Conversely, dye loading could perturb $[Mg^{2+}]_i$ or chelate heavy metals that are important in cell functions.

Thus there is a need for a new class of fluorescent indicator dyes that are specific for calcium ions. Such dyes are needed to measure calcium concentrations in aqueous solutions, especially biological fluids and even more especially, calcium concentrations within living cells. To allow measurement of calcium concentrations on an absolute scale, the new fluorescent indicator compounds should exhibit a wavelength shift upon $Ca^{2+}$-binding. The new compounds should also overcome some of the specific problems associated with use of the known Ca-specific indicator, quin2. More specifically, as compared to quin 2, the new compounds should show much stronger fluorescence, a somewhat weaker affinity for $Ca^{2+}$ and a better selectivity against magnesium and heavy metals.

OBJECTS OF THE INVENTION

It is an object of the present invention to provide a new class of fluorescent, calcium-specific indicators.

It is a further object of the present invention to provide a new class of fluorescent, calcium-specific indicator compounds that will measure calcium concentrations in aqueous solutions.

It is a further object of the present invention to provide a new class of fluorescent, calcium-specific indicator compounds that will measure calcium concentrations in biological fluids.

It is a further object of the present invention to provide a new class of fluorescent, calcium-specific indicator compounds that will measure calcium concentrations within living cells.

It is a further object of the present invention to provide a new class of fluorescent, calcium-specific indicator compounds that show a strong fluorescence in both the $Ca^{2+}$ bound and unbound states.

It is a further object of the present invention to provide a new class of fluorescent, calcium-specific indicators that exhibit a wavelength shift upon $Ca^{2+}$-binding.

It is a further object of the present invention to provide fluorescent, calcium-specific indicator compounds that will measure calcium at micromolar levels.

It is a further object of the present invention to provide fluorescent, calcium-specific indicator compounds that exhibit a good selectivity against magnesium and heavy metals.

It is a still further object of the present invention to provide an improved method for synthesizing alpha-acyloxyalkyl bromide.

It is a still further object of the present invention to provide an improved method for synthesizing alpha-acetoxymethyl bromide.

It is a still further object of the present invention to provide an improved method for synthesizing alpha-acyloxyalkyl bromides wherein the bromides so synthesized are free of contaminating bis(1-bromoalkyl) ether.

Other objects of the invention will become apparent to those skilled in the art from the following description, taken in connection with the accompanying drawings.

DETAILED DESCRIPTION OF THE DRAWINGS

Figure 1:
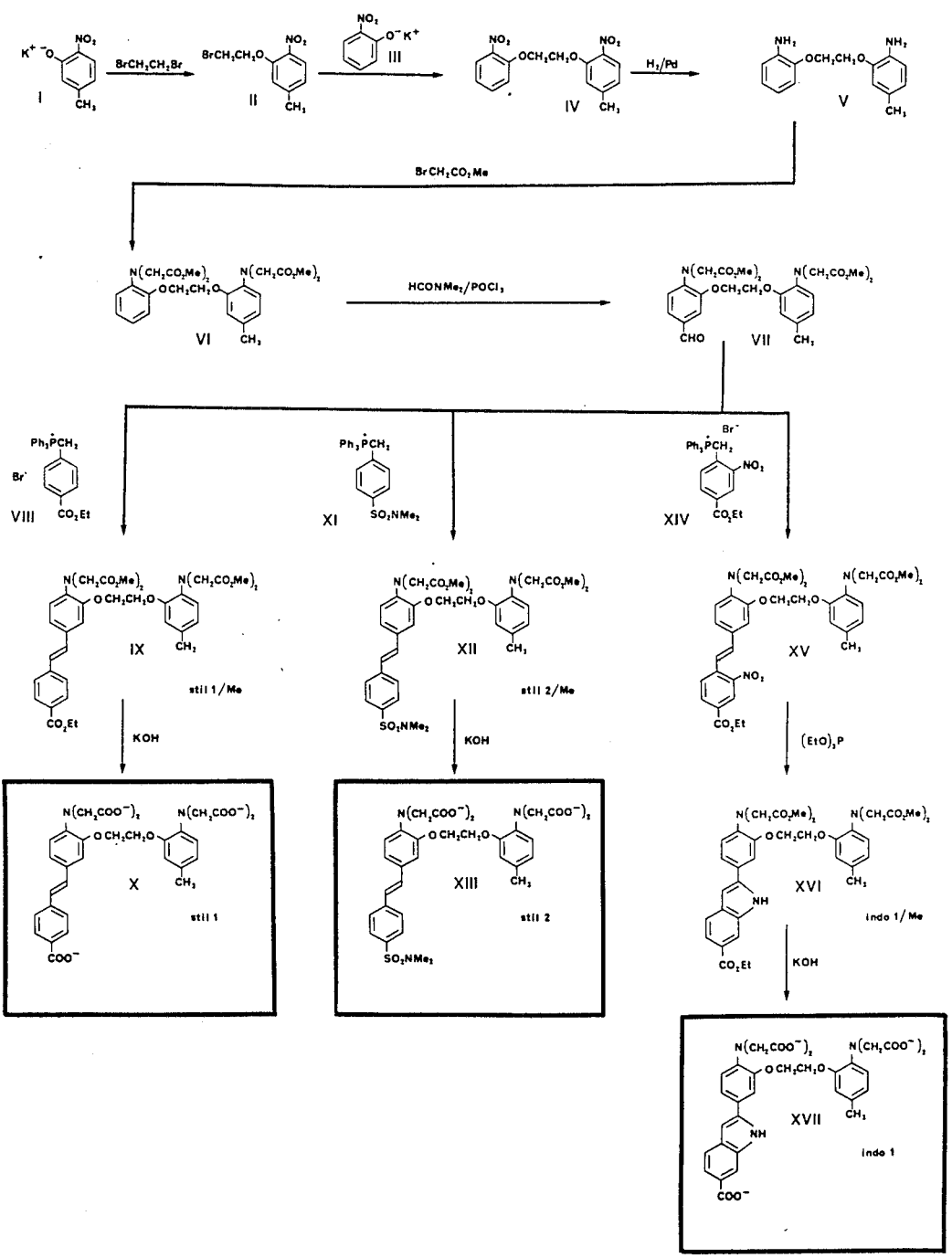
FIG. 1 is a chemical flow chart illustrating the synthetic pathway leading to stil-1, stil-2, and indo-1.

FIG. 1 shows the synthetic pathway leading to stil-1, stil-2, and indo-1. The Roman numerals used in the figure are keyed to the synthetic details discussed in the METHODS OF SYNTHESIS section, infra.

Figure 2:
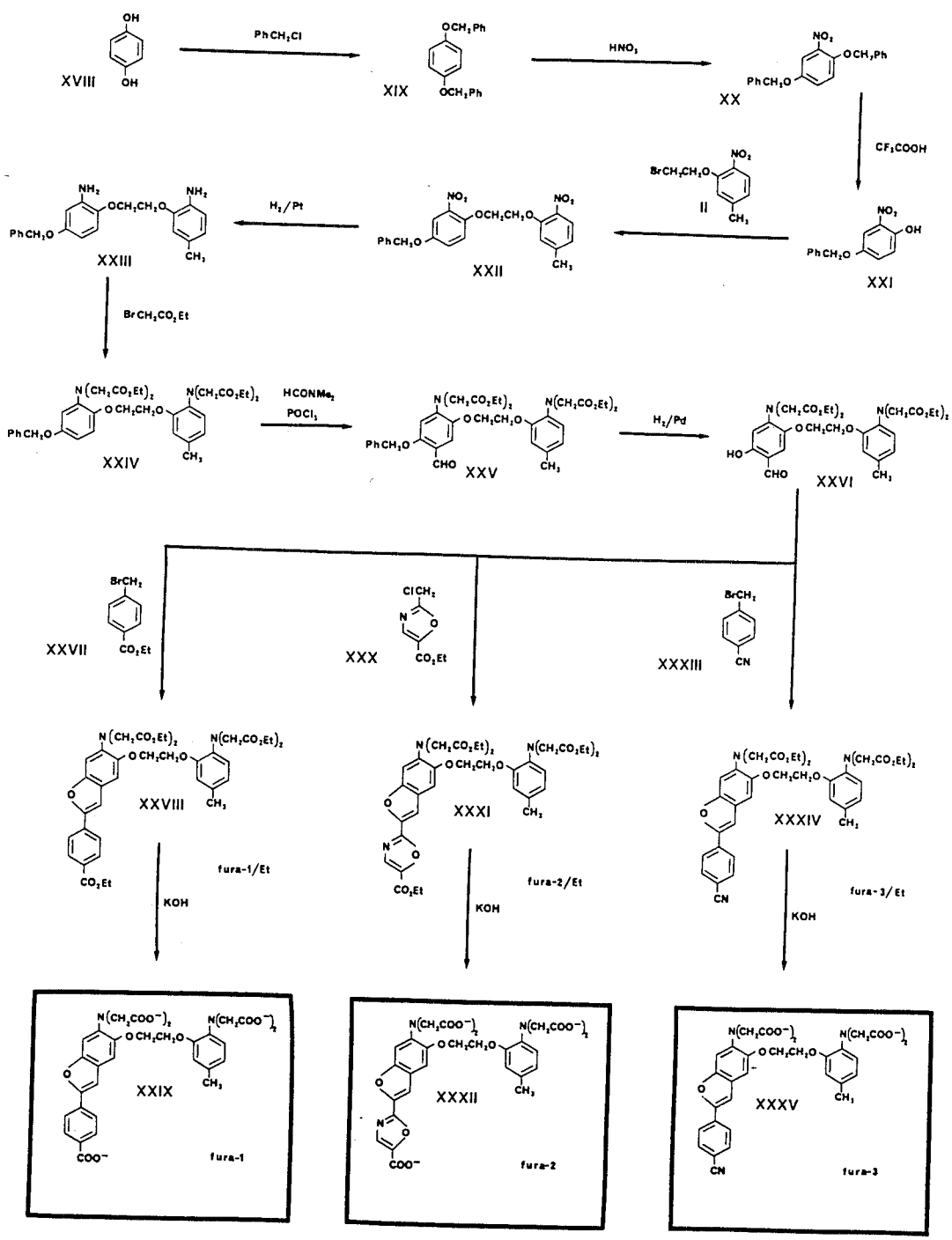
FIG. 2 is a chemical flow chart illustrating the synthetic pathway leading to fura-1, fura-2, and fura-3.

FIG. 2 shows the synthetic pathway leading to fura-1, fura-2, and fura-3. Again, the Roman numerals used in the figure are keyed to the synthetic details discussed in the METHODS OF SYNTHESIS section, infra.

Figure 3:
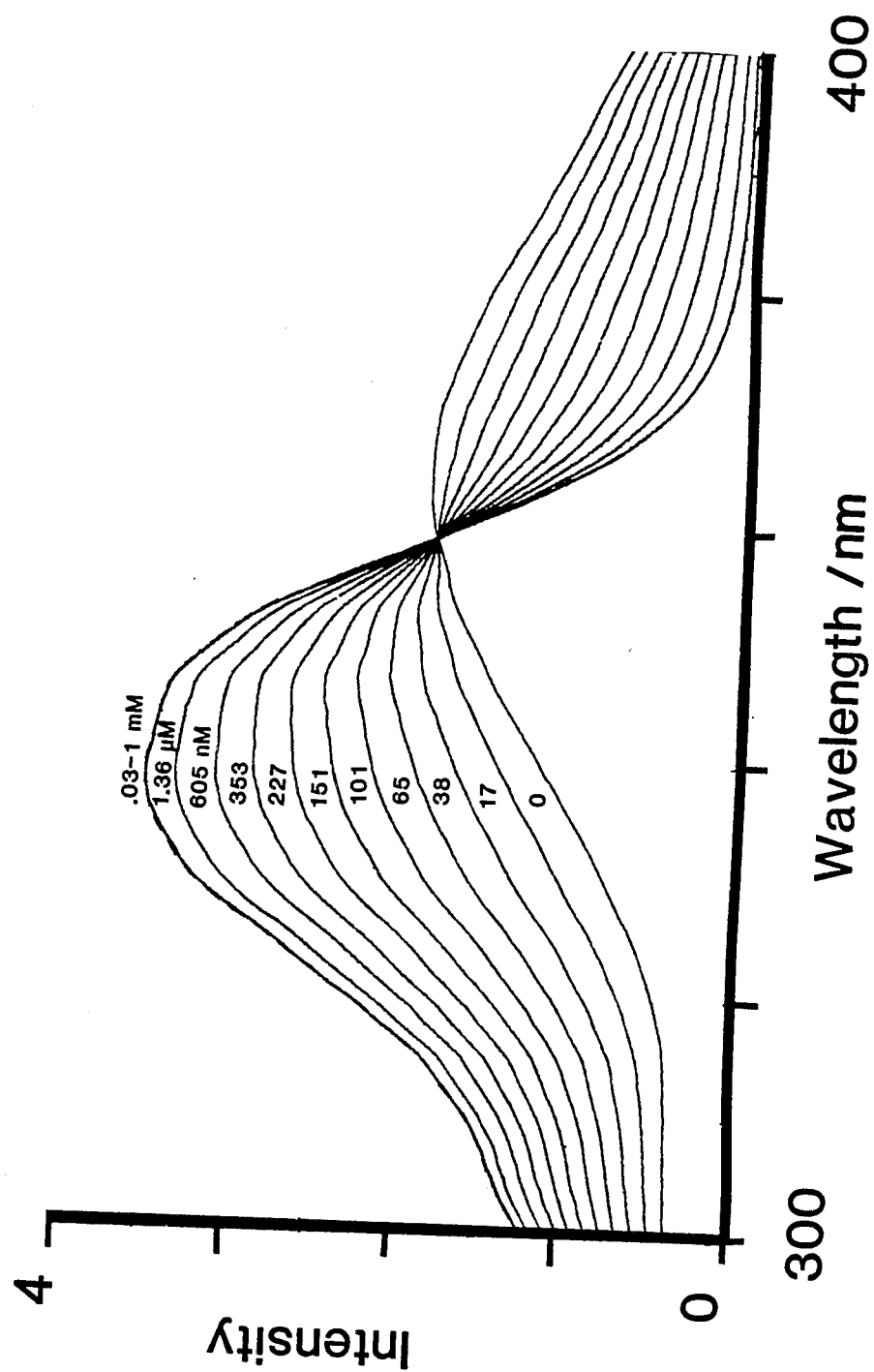
FIG. 3 is a graph showing a family of excitation spectra for fura-2 at 20° in buffers with free $Ca^{2+}$ values ranging from <1 nM to >10 microM.

FIG. 3 shows a family of excitation spectra for 1 microM fura-2 at 20° C. in buffers with free $Ca^{2+}$ values ranging from <1 nM to >10 microM. The excitation bandwidth was 1.9 nm, the emission was collected at 510 nm with 4.6 nm bandwidth, and the spectra were automatically corrected for excitation lamp and monochromator characteristics using a rhodamine B quantum counter. The titration was done starting with 5 ml of 100 mM KCl, 10 mM KMOPS, 10 mM $K_2H_2EGTA$, 1 microM fura-2, adjusting the pH to 7.20, recording the spectrum, then discarding 0.5 ml of this solution and replacing with 0.5 ml of 100 mM KCl, 10 mM KMOPS, 10 mM $K_2CaEGTA$, 1 microM fura-2, readjusting the pH to 7.20, and recording the spectrum which was then in 9 mM $K_2H_2EGTA$ and 1 mM $K_2CaEGTA$. Subsequent iterations to reach n mM CaEGTA, (10−n) mM EGTA, n=2-10, were done by discarding 5.0/(11−n) ml and replacing with equal volumes of the 10 mM $K_2CaEGTA$ −1 microM fura-2 stock. After n=10 had been reached to give a free $Ca^{2+}$ between $10^{-4}$ and $10^{-5}$ M, addition of 1 mM $CaCl_2$ had no further effect on the spectrum. Equality of Ca and EGTA contents in the $K_2CaEGTA$ solution was insured by titration of $K_2H_2EGTA$ with $CaCl_2$ to the potentiometric endpoint measured with a $Ca^{2+}$-selective electrode. EGTA was Fluka Chemical "puriss" grade.

Figure 4:
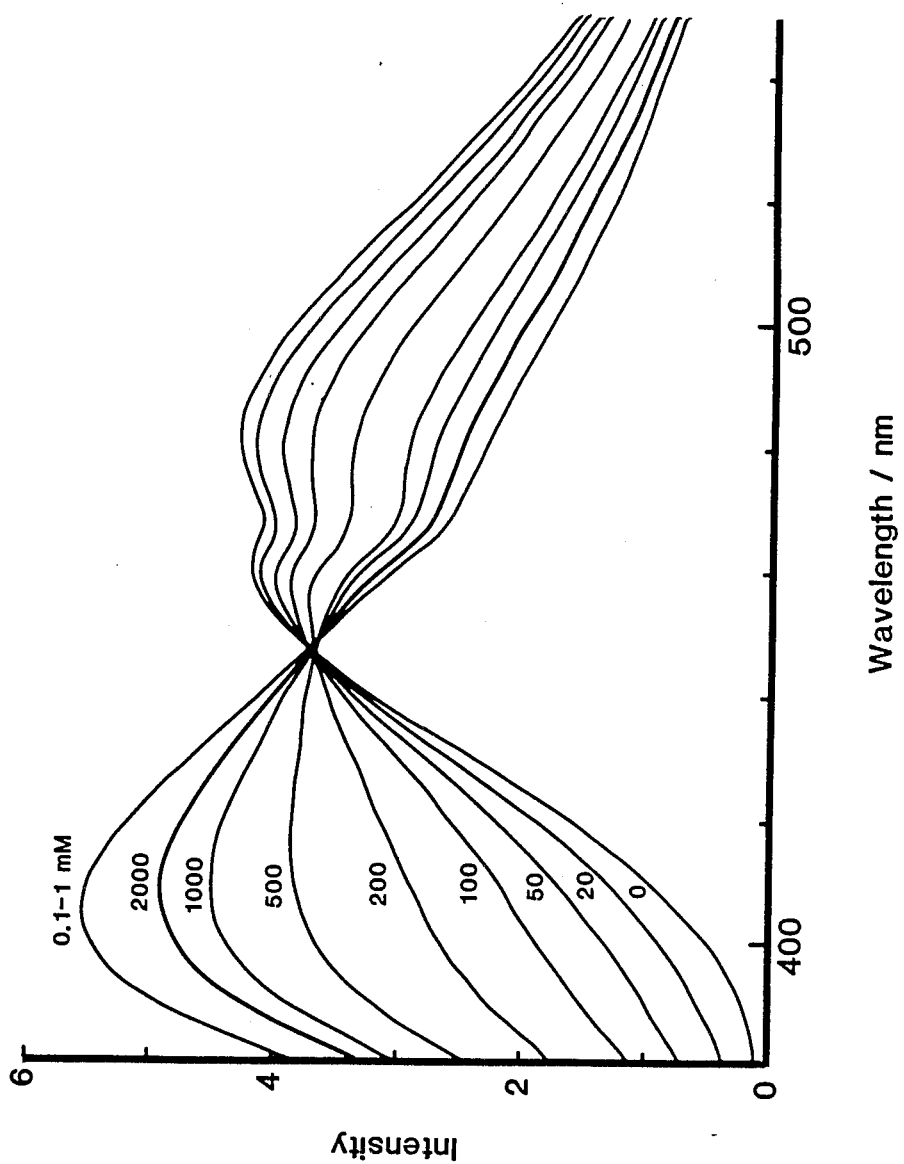
FIG. 4 is a graph showing emission spectra for indo-1 as a function of free $Ca^{2+}$.

FIG. 4 shows emission spectra for indo-1 as a function of free $Ca^{2+}$. The dye, 6 microM, was titrated in 115 mM KCl, 20 mM NaCl, 10 mM MOPS, 1.115 mM $MgCl_2$, 1.115 mM $K_2H_2EGTA$, KOH to pH 7.050±0.004, 37° C., to which small aliquots of $K_2CaEGTA$ were added from a micrometer syringe to raise free $Ca^{2+}$ to the values labeling each curve, in units of nM unless otherwise specified. Excitation was at 355 nm, and both excitation and emission were set to 5 nm bandwidth. These spectra are not corrected for the emission sensitivity characteristics of the Perkin Elmer MPF-44; in particular the notch at 465 nm is an instrumental artifact. Corrected emission spectra show the low-Ca 485 nm peak to be of very similar amplitude to the high-Ca 404 nm peak when excitation is at 355-356 nm.

Figure 5:
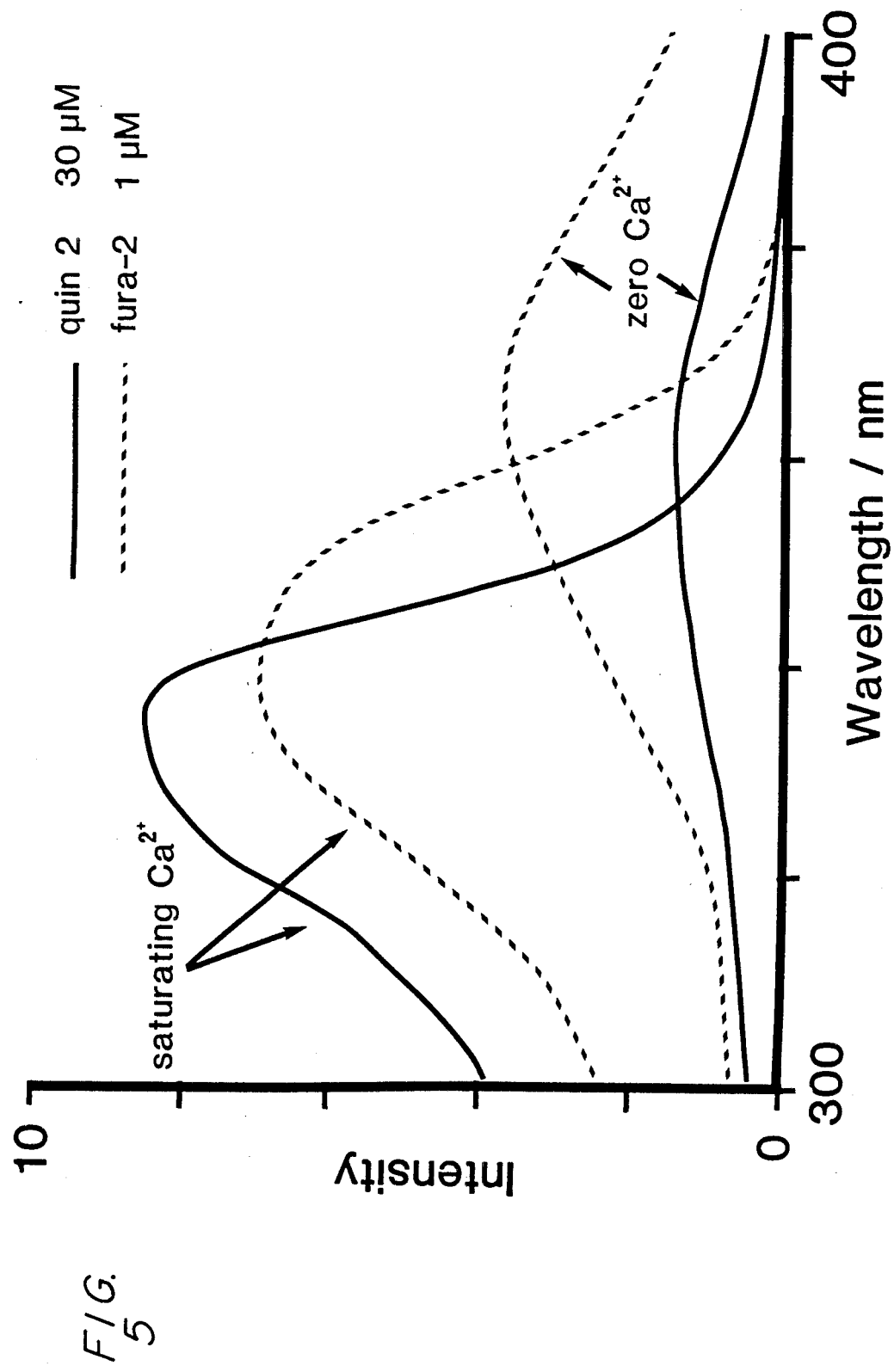
FIG. 5 is a graph showing excitation spectra for 1 microM fura-2 and 30 microM quin2 under identical sets of conditions.

FIG. 5 shows excitation spectra of 1 microM fura-2 and 30 microM quin-2 under identical sets of conditions: 130 mM KCl, 10 mM MOPS, 1 mM EDTA, KOH to pH 7.20, 20° C., before and after addition of 2 mM $CaCl_2$ to give 1 mM free $Ca^{2+}$. Emission was collected at 500 nm, 4.6 nm bandwidth, and the excitation bandwidth was 0.93 nm. Quin2 free acid was from Lancaster Synthesis, Morecambe, England.

Figure 6:
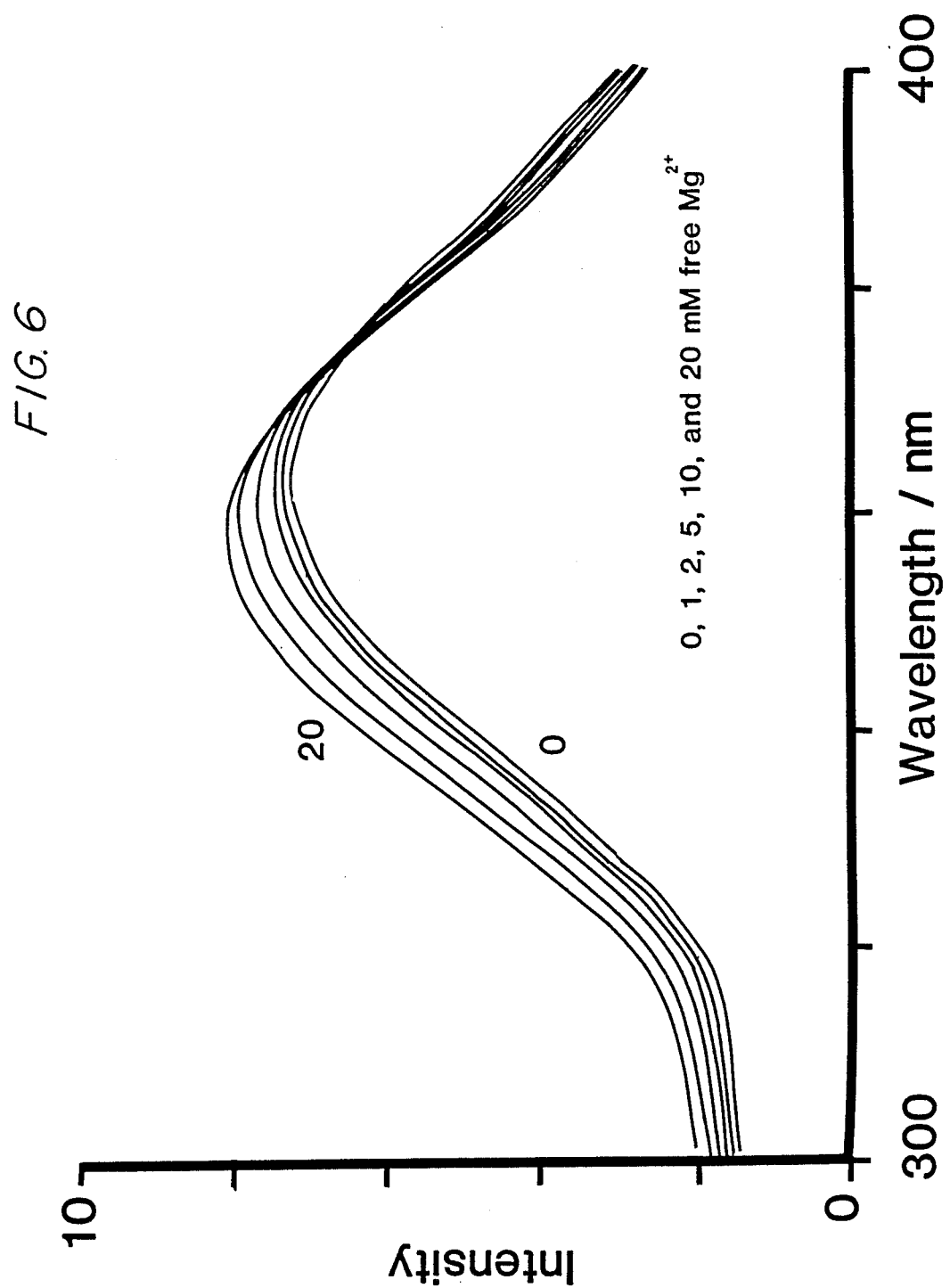
FIG. 6 is a graph showing the effect of $Mg^{2+}$ on fura-2.

FIG. 6 shows the effect of $Mg^{2+}$ on fura-2. An excitation spectrum was recorded of 2 microM fura-2 in 2.5 ml 32 mM KCl, 1 mM EGTA, 10 mM MOPS, adjusted with KOH to pH 7.18 while thermostatted at 20° C. Then 25 microliters of this solution was discarded and replaced by 25 microliters of a solution containing 2 microM fura-2, 104.8 mM $MgCl_2$, 5.8 mM EGTA, 10 mM MOPS, adjusted with KOH to pH 7.18. Since both stocks had 1 mM free EGTA but the latter had 100 mM free Mg, the 99:1 v/v composite went to 1.0 mM free $Mg^{2+}$. Further iterations attained 2, 5, 10, and 20 mM free $Mg^{2+}$ by successively discarding 25.25, 76.53, 131.6, and 277.8 microliters of the mixture and replacing each with an equal volume of the high-Mg stock. Emission was collected at 510 nm, 4.6 nm bandpass, and excitation 0.9 nm bandpass.

Figure 7:
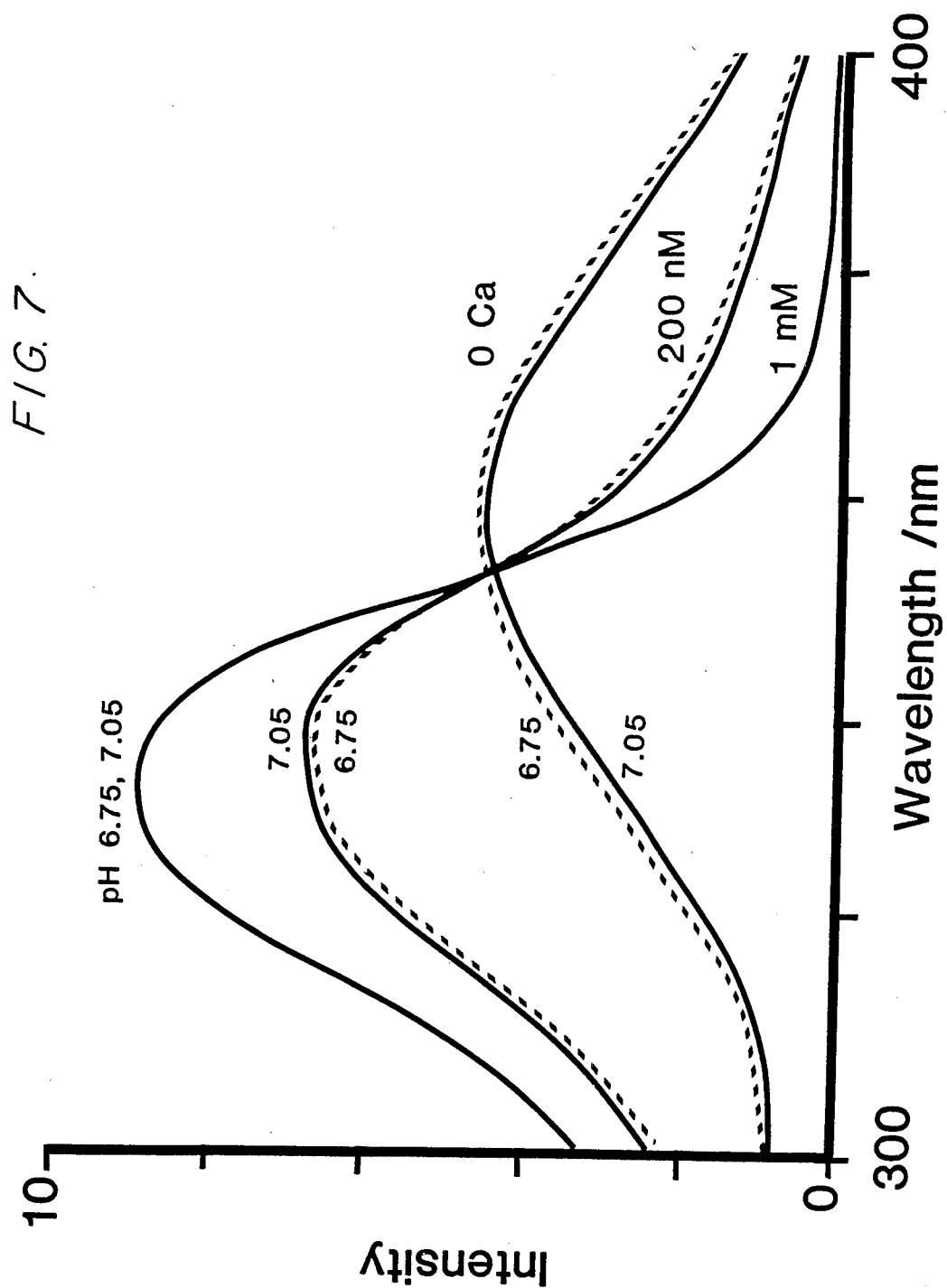
FIG. 7 is a graph showing the effect of pH excursion between 6.75 and 7.05 on fura-2 at zero, 200 nM and 1 mM free $Ca^{2+}$.

FIG. 7 shows the effect of pH excursion between 6.75 and 7.05 on fura-2 at zero, 200 nM, and 1 mM free $Ca^{2+}$. An excitation spectrum of 0.5 microM fura-2 was recorded in 135 mM KCl, 5 mM MOPS, 2 mM EGTA, adjusted with KOH to pH 7.05 at 37°. The succeeding spectra were taken following acidification with HCl to pH 6.75; addition of 0.379 mM $CaCl_2$ and KOH to pH 6.75; addition of 0.655 mM more $CaCl_2$ and KOH to pH 7.05; addition of 2 mM $CaCl_2$ and KOH to pH 6.75; KOH to pH 7.05. A record was kept of the volumes added, so that the spectra shown have been scaled to compensate for the slight dilution effects. Emission was collected at 505 nm, 18.5 nm bandpass, with 4.6 nm excitation bandpass. The curves with 200 nM free Ca were important to include because there might have been an important protonation, perhaps on the amino nitrogen of the right hand ring, that would significantly inhibit $Ca^{2+}$ binding without affecting the fluorescence in either zero $Ca^{2+}$ or overwhelmingly high $Ca^{2+}$. The observation that at 200 nM $Ca^{2+}$ the pH 6.75 curve is closer than the pH 7.05 to the "O Ca" curve suggests that such an $H^+$ inhibition of $Ca^{2+}$ binding does take place to a small extent, but the effect is clearly small and is partly neutralized by the slight direct effect of pH on the $Ca^{2+}$-free dye.

DEFINITION OF TERMS USED HEREIN

As used herein, $[Ca^{2+}]_i$ means intracellular free calcium.

As used herein, EGTA means ethylene glycol bis(-beta-aminoethyl ether)-N,N,N',N'-tetracetic acid.

As used herein, BAPTA means 1,2-bis(2-aminophenoxy)ethane N,N,N',N'-tetraacetic acid; the chemical structure for BAPTA is:

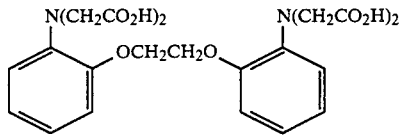

As used herein, BAPTA-like means substituted derivatives of BAPTA which retain the essential characteristic of two bis(carboxymethyl)amino-substituted phenyl rings, said rings being linked at the positions ortho to the amines through a four atom bridge wherein the atom adjacent to each phenyl ring is N or O and the two center atoms are each C. By this definition, it is apparent that "BAPTA-like" includes compounds like quin-1 and quin-2.

As used herein, quin1 means 2-[[2-[bis(carboxymethyl)amino]-5-methylphenoxy]methyl]-8-[bis(carboxymethyl)amino]-quinoline.

As used herein, quin2 means 2-[[2-[bis(carboxymethyl)amino]-5-methylphenoxy]-6-methoxy-8-[bis(carboxymethyl)amino]quinoline; the chemical structure for quin2 is:

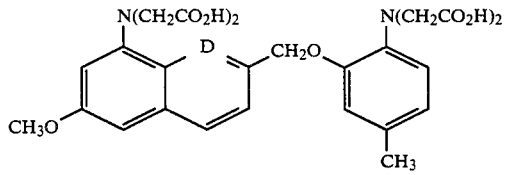

As used herein MOPS means 3-(N-morpholino)propanesulfonic acid.

As used herein, stil-1 means 1-(2-amino-5-[(2-(4-carboxyphenyl)-E-ethenyl-1-]phenoxy)-2-(2'-amino-5'-methylphenoxy)ethane-N,N,N',N'-tetraacetic acid. The chemical structure for stil-1 is shown in FIG. 1 as compound X.

As used herein, stil-2 means 1-(2-amino-5-[(2-(4-N,N-dimethylaminosulfonylphenyl)-E-ethenyl-1-]phenoxy)2-(2'-amino-5'-methylphenoxy)ethane-N,N,N', N'-tetraacetic acid. The chemical structure for stil-2 is shown in FIG. 1 as compound XII.

As used herein, indo-1 means 1-(2-amino-5-[6-carboxyindolyl-2]-phenoxy)-2-(2'-amino-5'-methylphenoxy)ethane-N,N,N',N'-tetraacetic acid. The chemical structure for indo-1 is shown in FIG. 1 as compound XVII.

As used herein, fura-1 means 1-(2-(4-carboxyphenyl)-6-amino-benzofuran-5-oxy)-2-(2'-amino-5'-methylphenoxy)ethane-N,N,N',N'-tetraacetic acid. The chemical structure for fura-1 is shown in FIG. 2 as compound XXIX.

As used herein, fura-2 means 1-(2-(5'-carboxyoxazol-2'-yl)-6-aminobenzofuran-5-oxy)-2-(2'-amino-5'-methylphenoxy)ethane-N,N,N',N'-tetraacetic acid. The chemical structure for fura-2 is shown in FIG. 2 as compound XXXV.

As used herein, fura-3 means 1-(2-(4-cyanophenyl)-6-aminobenzofuran-5-oxy)-2-(2'-amino-5'-methylphenoxy)ethane-N,N,N',N'-tetraacetic acid. The chemical structure for fura-3 is shown in FIG. 2 as compound XXXII.

As used herein, pharmaceutically acceptable esters mean those readily hydrolyzable esters which are known and used in the pharmaceutical industry, especially alpha-acyloxyalkyl esters. See generally, references 37 and 38.

As used herein, pharmaceutically acceptable nontoxic salts mean carboxylic acid salts wherein the counterion or ions are all Na, K, $NR_4^+$ (where R=H, $C_1$-$C_4$ alkyl or a mixture thereof), Ca, or Mg, or some combination of these counterions, or some combination of acid salts of these counterions plus free acid groups.

As used herein, microM means micromolar.

Temperatures herein are given in degrees Centigrade.

For use herein, "dye" and "indicator" are used interchangeably.

The chemical formulas for compounds shown in FIGS. 1 and 2 are identified with Roman numerals. These Roman numerals are used throughout the specification (see especially, the METHODS OF SYNTHESIS section, infra) to identify compounds that correspond to those shown in the figures.

The new dyes disclosed herein are named with hyphens to distinguish the number 1 from the letter l, e.g., indo-1, fura-1, fura-2, stil-1, stil-2, etc.

REFERENCE LIST

The scientific publications cited herein are expressly incorporated by reference.

1. Blinks, J. R., Wier, W. G., Hess, P. and Prendergast, F. G. (1982), *Progr. Biophys. Molec. Biol.*, 40, 1–114.
2. Tsien, R. Y. and Rink, T. J. (1983) in *Current Methods in Cellular Neurobiology* (Barker, J. L. and McKelvy, J. F., eds.) Vol. III, pp. 249–312, Wiley, New York.
3. Campbell, A. K. (1983), *Intracellular Calcium*, Wiley, New York.
4. Tsien, R. Y. (1983), *Ann. Rev. Biophys. Bioeng.*, 12, 91–116.
5. Tsien, R. Y., Pozzan, T. and Rink, T. J. (1984), *Trends Biochem. Sci.*, pp. 263–266.
6. Tsien, R. Y. (1980), *Biochemistry*, 19, 2396–2404.
7. Tsien, R. Y., Pozzan, T. and Rink, T. J. (1982), *J. Cell Biol.*, 94, 325–334.
8. Arslan, P., diVirgilio, F., Tsien, R. Y. and Pozzan, T., Manuscript submitted for publication to *J. Biol. Chem.*

9. Lippert, E., Naegele, W., Seibold-Blankenstein, I., Staiger, Y. and Voss, W. (1959), *Fresenius' Z. Anal. Chem.*, 170, 1–18.
10. Miller, N. N., ed. (1981), *Standards in Fluorescence Spectrometry*, Champman and Hall, London.
11. Martell, A. E. and Smith, R. M. (1974), *Critical Stability Constants*, Vol. 1, Plenum Press, New York.
12. Tsien, R. Y. and Rink, T. J. (1980), *Biochem. Biophys. Acta.*, 599, 623,638.
13. DiPolo, R., Requena, J., Brinley, F. J., Jr., Mullins, L. J., Scarpa, A., Tiffert, T. (1976), *J. Gen. Physiol.*, 67, 433–467.
14. Owen, J. D. (1976), *Biochem. Biophys. Acta.*, 451, 321–325.
15. Zucker, R. S. and Steinhardt, R. A. (1979), *Nature*, 279, 820.
16. Baker, P. F. and Whitaker, M. J. (1979), *Nature*, 279, 820–821.
17. Harafuji, H. and Ogawa, Y. (1980), *J. Biochem. (Tokyo)*, 87, 1305–1312.
18. Rossotti, H. (1978), *The Study of Ionic Equilibria*, Longman, London.
19. Cadogan, J. I. G. (1979), in *Organophosphorus Reagents in Organic Synthesis* (Cadogan, J. I. G., ed.), pp. 269–294, Academic Press, New York.
20. Marsh, J. P., Jr. and Goodman, L. (1965), *J. Organic Chem.*, 30, 2491–2492.
21. Freifelder, M. (1971), *Practical Catalytic Hydrogenation*, Wiley, New York.
22. Yamawaki, J., Kawate, T., Ando, T. and Hanafusa, T. (1983), *Bull. Chem. Soc. Jpn.*, 56, 1885–1886.
23. Tsien, R. Y. (1981), *Nature*, 290, 527–528.
24. Neuenschwander, M. and Iseli, R. (1977), *Helvetica Chimica Acta.*, 60, 1061–1072.
25. Ross, D. L. and Blanc, J. (1971), in *Photochromism* (Techniques of Chemistry, Vol. III), (Brown, G. H., ed.), pp. 471–556, Wiley, New York.
26. Hesketh, T. R., Smith, G. A., Moore, J. P., Taylor, M. V. and Metcalfe, J. C. (1983), *J. Biol. Chem.*, 258, 4876–4882.
27. Williams, R. J. P. (1982), *FEBS Lett.*, 140, 3–10.
28. Rogers, J., Hesketh, T. R., Smith, G. A., Beaven, M. A., Metcalfe, J. C., Johnson, P. and Garland, P. B. (1983), *FEBS Lett.*, 161, 21–27.
29. Rink, T. J., Tsien, R. Y. and Pozzan, T. (1982), *J. Cell Biol.*, 95, 189–196.
30. Titley, A. F. (1928), *J. Chem. Soc.*, pp. 2571–2583.
31. Quackenbush, F. W., Grogan, W. M., Jr., Midland, S. L., Bell, F. P., MacNintch, J. E., Hutsell, T. C., Cruzan, G., Klauda, H. C. (1977), *Artery* (Leonidas, Mich.), 3, 553–575.
32. *Beilsteins Handbuch der Organisches Chemie*, (1967), Drittes Erganzungswerk, Vol. 6, p. 4402, Springer Verlag, Berlin.
33. Schiff, H. and Pellizzari, G. (1883), *Liebigs Annalen der Chemie*, 221, 365–379.
34. Alonso, M. and Jano, P. (1980), *J. Heterocyclic Chem.*, 17, 721–725.
35. Knoevenagel, E. (1913), *Liebigs Annalen der Chemie*, 402, 111–148.
36. Sayce, I. G. (1968), *Talanta*, 15, 1397–1411.
37. Ferres, H. (7 June 1980), *Chem. Ind.*, p. 435–440.
38. Wermuth, C. G. (7 June 1980), *Chem. Ind.*, p. 433–435.
39. Schmitdt, A. H. (1981), *Aldrichimica Acta*, 14, 31–38.

BRIEF DESCRIPTION OF THE INVENTION

The present invention comprises a new class of fluorescent, calcium-specific indicator dyes that combines a stilbene-type fluorophore with a tetracarboxylate $Ca^{2+}$ chelating compound having the octacoordinate ligating groups characteristic of EGTA and BAPTA.

In a first form the new dyes are comprised of a BAPTA-like $Ca^{2+}$ chelator coupled to a single fluorescent dye. In this form the new dyes are comprised of a bis(2-aminophenoxy)ethane-N,N,N',N'-tetraacetic acid having the generic formula:

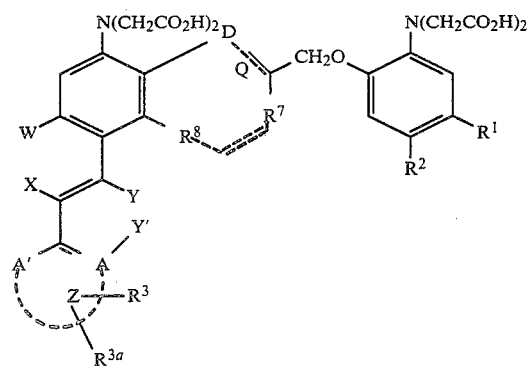

and the pharmaceutically acceptable non-toxic salts and esters thereof wherein:

$R^1$ is selected from the group comprised of —H, —$CH_3$, —F, —Cl, and —Br;

$R^2$ is selected from the group comprised of —H, —$CH_3$, —F, —Cl, —Br, and $C_0$–$C_4$ alkoxy;

$R^3$ or $R^{3a}$ are independently H or a polar, electron withdrawing function selected from the group comprised of —$CO_2H$, —$CO_2R^4$, —$CONR^5R^6$, —$SO_3H$, —$SO_2NR^5R^6$, —$SO_2CF_3$, —$COCH_3$, and —CN, or $R^3$ and $R^{3a}$ together are —(CO)$NR^5$(CO)—;

$R^4$ is alpha-acyloxyalkyl or a pharmaceutically acceptable esterifying group;

$R^5$ and $R^6$ are independently —H, methyl, or ethyl;

Z is an aromatic or heteroaromatic system coupled to the 5 position of one 2-aminophenoxy ring through a trans ethylenic linkage, wherein said ethylenic linkage may itself be part of an aromatic heteroaromatic ring system;

W is H and X is H; or

W and X together are O, or $NR^5$;

Y is H; Y' is H (unless A is $NR^5$, O, or S); or

Y and Y' together are $NR^5$ and A is C;

A and A' are independently C, N, O, or S;

D is O, N, NH, or N alkyl;

Q is a double bond when D is N and a single bond otherwise; and $R^7$ is H and $R^8$ is H or $R^7$ and $R^8$, together with heteroatom D, the carbon adjacent $R^7$, and the phenyl ring adjacent to $R^8$, form a quinoline ring system (D=N, Q=double bond).

In a second form the new dyes are comprised of a BAPTA-like $Ca^{2+}$ chelator coupled to a pair of fluorescent dyes. In this form the new dyes are comprised of a compound having the generic formula:

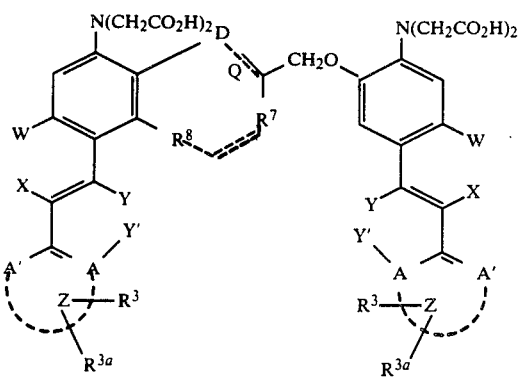

and the pharmaceutically acceptable non-toxic salts and esters thereof wherein:

$R^3$ or $R^{3a}$ are independently H or a polar, electron withdrawing function selected from the group comprised of —$CO_2H$, —$CO_2R^4$, —$CONR^5R^6$, —$SO_3H$, —$SO_2NR^5R^6$, —$SO_2CF_3$, —$COCH_3$, and —CN, or $R^3$ and $R^{3a}$ together are —(CO)$NR^5$(CO)—;

$R^4$ is alpha-acyloxyalkyl or a pharmaceutically acceptable esterifying group;

$R^5$ and $R^6$ are independently —H, methyl, or ethyl;

Z is an aromatic or heteroaromatic system coupled to the 5 position of one 2-aminophenoxy ring through a trans ethylenic linkage, wherein said ethylenic linkage may itself be part of an aromatic heteroaromatic ring system;

W is H and X is H; or
W and X together are O, or $NR^5$;
Y is H; Y' is H (unless A is $NR^5$, O, or S); or
Y and Y' together are $NR^5$ and A is C;
A and A' are independently C, N, O, or S;
D is O, N, NH, or N alkyl;
Q is a double bond when D is N and a single bond otherwise; and
$R^7$ is H and $R^8$ is H or
$R^7$ and $R^8$, together with heteroatom D, the carbon adjacent $R^7$, and the phenyl ring adjacent to $R^8$, form a quinoline ring system (D=N, Q=double bond).

Preferred indicators in both the first and second forms contain heterocyclic bridges to restrict the ethylenic bond of the stilbene to the trans configuration and to reduce hydrophobicity.

In addition the present invention comprises an improved method for synthesizing alpha-acyloxyalkyl bromides, especially acetoxymethyl bromide which is useful in preparing the acetoxymethyl esters contained within the class of new indicators disclosed and claimed herein. Alpha-acyloxyalkyl bromides are useful to the pharmaceutical industry in the preparation of prodrugs (see references 38 and 39). The improved method comprises reacting approximately 1 equivalent of 1,1-diacyloxyalkane and approximately 1 to 1.5 equivalents of trimethylsilyl bromide, in the presence of approximately 0.1 to 0.2 equivalents of a Lewis acid catalyst, in a reaction vessel with stirring until the reaction is complete, and then recovering the alpha-acyloxyalkyl bromides so produced.

Alpha-acyloxyalkyl bromides produced by known methods are contaminated with bis(1-bromoalkyl) ether. Alpha-acyloxyalkyl bromides produced by the improved method of the present invention are free of contaminating bis(1-bromoalkyl) ether. Also, the new method is capable of making certain alpha-acyloxyalkyl bromides that would be extremely difficult or impossible to make by known methods because those known methods require pure anhydrous aldehydes that are hygroscopic, unstable, and prone to polymerization.

DETAILED DESCRIPTION OF THE INVENTION

The present invention comprises a new class of fluorescent, calcium-specific indicator dyes that combines a stilbene-type fluorophore with analogs of the octacoordinate tetracarboxylate $Ca^{2+}$ chelating compound, BAPTA. In a first form, the new dyes are comprised of a BAPTA analog coupled to a single fluorescent dye; in a second form, a BAPTA analog is coupled to a pair of fluorescent dyes. Preferred compounds in both the first and second forms contain heterocyclic bridges to restrict the ethylenic bond of the stilbene to the trans configuration.

The new indicator dyes disclosed herein have in common at least one stilbene-type functionality attached to at least one of the aromatic rings in the parental BAPTA-like compound. This stilbene-type of function consists of an aromatic or heteroaromatic system that is coupled to a parental (BAPTA-like) aromatic ring through two carbons containing a trans double bond. A typical final compound has spectral contributions from both the chelating BAPTA-like portion of the molecule (e.g., lambda max=ca. 254 nm, extinction coefficient=ca. 16,000) (see reference 6) and the fluorophore (e.g., lambda max>300 nm, extinction coefficient>10,000) see Table 1, infra. Since the fluorophore is electronically coupled to the chelator, when calcium is bound by the molecule, the chelating portion of the molecule no longer donates electron density to the fluorophore portion, causing a decrease in maximum wavelength of absorbance. As long as there is no more than one sigma bond in a row in the link between fluorophore and BAPTA-like chelator, this electrical coupling will be maintained. The link between the fluorophore and chelator portions can also be part of a complex heterocycle, which in turn can be part of the fluorophore or part of the chelator.

It is known that cation affinities of BAPTA derivatives can be increased or decreased by appropriate electron-donating or electron-withdrawing substituents (see generally reference 6). For example, substitution of two methyl groups for the two hydrogens para to the two nitrogens of BAPTA strengthened $Ca^{2+}$ binding by 0.4 log unit and similar disubstitution with bromine weakened $Ca^{2+}$ binding by 1.2 log units (see reference 6). We have found that monosubstitution gives half as much effect on calcium affinity (data not shown). Those skilled in the art will realize that the effect of other substituents on the cation affinities of the present compounds should be quantitatively predictable by a Hammett-type linear free-energy relation.

It is also known that the greatest change in dye indicating characteristics occurs within 2 log [$Ca^{2+}$] units of the $K_d$ of any particular dye (see reference 6). As a result it would be helpful to have dyes available which have a range of $K_d$'s. To this end, $R^1$ and $R^2$ can be varied to adjust the $K_d$ up or down. As expected, the dye component of the molecule weakens $Ca^{2+}$ binding by 0–0.3 log units (compare $K_d$'s in Table 1 with BAPTA $K_d$=100 nm, see reference 6).

In the preparation of compounds containing only one long-wavelength fluorophore, if $R^2$ is anything except hydrogen, the 5 position of that ring will be blocked and formylation can proceed only at the desired 5 position of the 4-W-benzene ring or equivalent quinoline. If $R^2$ is hydrogen, the presence of halogen at $R^1$ will deactivate that ring for electrophilic substitution and formylation will occur mainly at the desired position. Even if $R^2=H$ and $R^1=H$ or alkyl, the desired product can be prepared by controlled formylation and separation of the desired product or by beginning the synthesis with an appropriate 3-hydroxy-4-nitrobenz- aldehyde (see METHODS OF SYNTHESIS section, *infra*).

To prepare compounds containing two fluorophores, $R^2$ must be hydrogen and $R^1$ can be hydrogen, alkyl or any variation of substituent W. In this case, the desired formylation occurs at the 5 position of both phenyl rings or the 5 position of both the $R^1$, $R^2$ phenyl and of the quinoline or benzopyran.

The dye component of the molecules is based on trans stilbene, but can take many other forms. The ethylene bridge of stilbene can be locked in the trans configuration by forming a heterocyclic ring which includes the bridge. Thus Y and Y' in the generic formulas shown in the BRIEF DESCRIPTION OF THE INVENTION section, *supra*, can together be a heteroatom, such as $NR^5$ and the dye molecule can be indole. The synthesis of such an indole is described *infra* in the METHODS OF SYNTHESIS section to illustrate this class of dye components (see indo-1). A heterocycle can also be formed which locks the ethylenic bridge to the phenyl ring of the chelating portion of the molecule. Thus if W and X (see generic formulas *supra*) are together $NR^5$, or O, a separate group of indole or benzofuran derivatives can be prepared. For exemplative purposes, synthesis of one such benzofuran is described *infra* in the METHODS OF SYNTHESIS section, (see compounds fura-1, fura-2 and fura-3).

The essential features of system Z are its aromaticity and connective relationship to the parent chelating compound. As shown in the generic formulas, the connection can be trans-ethylene or part of a heterocycle, as discussed above. For exemplative purposes, we describe in the METHODS OF SYNTHESIS section, *infra*, compounds which demonstrate use of phenyl or oxazole as Z, e.g. compounds stil-1 or fura-2, respectively, or, in conjunction with Y and $Y^1$ and the ethylenic bridge, indole as Z, e.g. compound indo-1.

The $R^3$ and $R^{3a}$ substituents of Z serve to increase the hydrophilicity of the aromatic, generally hydrophobic, dye component of the final molecule. $R^3$ and $R^{3a}$ also can be used to adjust somewhat the maximum absorbance or emission wavelength of the dye. A wide variety of $R^3$ and $R^{3a}$ substituents can be incorporated in the dyes disclosed and claimed in this invention, including the cyclic imide formed when $R^3$ and $R^{3a}$ together are $-(CO)NR^5(CO)-$. By way of example, use of carboxy, cyano, and aminosulfonyl for $R^3$ are illustrated (see synthesis of compounds fura-1, fura-3, and stil-2, respectively).

Methods for synthesizing the new dyes disclosed herein are outlined in the METHODS OF SYNTHESIS section, *infra*. Specific properties and embodiments of the new dyes, as exemplified by preferred forms indo-1, stil-1, stil-2, fura-1, fura-2 and fura-3, are disclosed and discussed in Examples I through VII, infra. More specifically, Example I discusses absorbance properties for the new indicators in the presence and absence of $Ca^{2+}$ while Example II discusses the fluorescence properties. Example III discloses $Ca^{2+}$ binding constants. Photoisomerization of the stilbene-type dyes is discussed in Example IV while cation selectivity is discussed in Example V. Example VI discusses membrane binding and Example VII discloses calibration equation for a dye using fluorescence intensity values at two wavelengths.

From the data disclosed and discussed in the various examples it can be seen that increased brightness of fluorescence is the most dramatically noticeable advantage of the new dyes as compared with their immediate predecessors such as quin2. The new dyes are ten to thirty-fold more strongly fluorescent, partly because of their five-to-six-fold higher extinction coefficients and partly because of their higher quantum efficiencies of fluorescence (up to 0.5 as compared with about 0.1 for quin2). The increased fluorescence means that far less dye needs to be introduced into a given amount of cells to get an adequate signal. The less dye inside the cells, the less likelihood there is of significantly buffering the calcium levels being measured or otherwise perturbing the cells. Alternatively, the increased brightness can permit $Ca^{2+}$ measurement in shorter observation times or from smaller volumes of tissue. An example of the latter is the observation with fura-2 (data not shown) of rises in $[Ca^{2+}]_i$ induced by mitogenic lectins of solitary thymocytes of about 6 microns diameter, a feat that had proven impossible with quin2 (see reference 28).

The next most important feature of the new dyes is the ability of $Ca^{2+}$ to significantly change the shape and wavelength distribution of the fluorescence spectra, not just the intensity. This wavelength shift makes it possible to measure calcium concentrations on an absolute scale simply from the ratio of fluorescences at two wavelengths, without consideration of dye concentration, optical pathlength, or absolute sensitivity of detection. (See Example VII.) All six of the preferred dyes (stil-1, stil-2, indo-1, fura-1, fura-2 and fura-3) disclosed herein as examples of the present invention have this feature in their excitation spectra. (Of the six, indo-1 is so far unique in also having a major change in emission wavelength upon binding calcium.) Existing dyes such as quin2 change intensity but not peak wavelength upon binding calcium, making their signals relatively difficult to calibrate. As a result they are not as useful as the new dyes disclosed herein for measuring calcium concentrations on an absolute scale by means of the wavelength ratio method.

Unfortunately the new dyes are only marginally better than existing dyes such as quin2 when it comes to the goals of increasing the wavelengths of excitation and emission and of weakening the $Ca^{2+}$ binding to permit exploration of higher $[Ca^{2+}]_i$ levels. Nevertheless, even the slightly longer excitation wavelengths for the new dyes as compared with the old (e.g. fura-2 compared with quin2) make it much easier to work with conventional fluorescence microscopes with glass optics that typically cut off very abruptly at wavelengths between 340 and 350 nm. The roughly two-fold higher dissociation constants for fura-2 and indo-1 compared to quin2 are expected to improve resolution of $[Ca^{2+}]_i$ levels above $10^{-6}M$.

For the new dyes, both the wavelengths and $Ca^{2+}$ dissociation constant should increase when groups more strongly electron-withdrawing than carboxylate are placed at the far end of the chromophore (compare fura-1 and fura-3). However, the terminal carboxylate is at least theoretically attractive as a deterrent of hydrophobic bonding of the long chromophore tail.

The large absorption coefficients of the new dyes are just as expected from the length of the chromophore and data on simpler analogs. Although quantum efficiencies cannot be predicted with certainty, extended chromophores with rigid ring structures are well known to be conducive to efficient fluorescence. The hypsochromic shift in absorption and excitation spectra upon binding $Ca^{2+}$ is well understood (see reference 6): the $Ca^{2+}$ monopolizes the lone pair of electrons on the main nitrogen, possibly by twisting the bond between the nitrogen and the ring. The conjugation between the lone pair and the rest of the chromophore is thereby disrupted. Presumably the $Ca^{2+}$ moves away from the nitrogen in the excited state, so that the emission wavelengths differ little between low and high $[Ca^{2+}]$. It is unclear why indo-1 should be an exception.

A fifth advantage of the new dyes over known dyes such as quin2 is their better selectivity for $Ca^{2+}$ over divalent cations such as $Mg^{2+}$, $Mn^{2+}$, $Zn^{2+}$ and $Fe^{2+}$. The improvements for fura-2 over quin2 are about three-fold, twelve-fold, and forty-fold for $Mg^{2+}$, $Mn^{2+}$, and $Zn^{2+}$ respectively. Most workers using quin2 have implicitly assumed that cytosolic free $Mg^{2+}$ was 1 mM as was measured in lymphocytes (see reference 7). If the true free $[Mg^{2+}]$ were 0 or 2 mM respectively, the true $\sim Ca^{2+}$ values would be about 0.5 or 1.5 times higher than those estimated assuming 1 mM $[Mg^{2+}]$. The new dyes should be less sensitive yet to uncertainties in $[Mg^{2+}]$. The only clear instance of heavy metal interference with quin2 has been in certain tumor cell lines (see reference 8). However the reduced heavy metal affinities of the new dyes should help guard against other occurrences as well as toxicity due to chelation of essential heavy metals. These dyes and quin2 might even be used as heavy metal indicators by working at the wavelengths where all the different $Ca^{2+}$ curves cross each other.

The improved divalent cation selectivity of the new dyes is probably due to the abandonment of the quinoline structure with its troublemaking ring nitrogen (see reference 6). Magnesium binding affects the spectrum much less than $Ca^{2+}$-binding probably because $Mg^{2+}$ is too small to bind to both amino nitrogens at once (see reference 6) and tends to choose the nitrogen on the right side of the structure as drawn, since that one is not in conjugation with the slightly electron-withdrawing chromophoric skeleton. Fura-2 and EGTA both respond to increasing temperature by weakening their $Ca^{2+}$ affinity and increasing their $Mg^{2+}$ affinity (see reference 11). This suggests that the thermodynamic bases for their $Ca^{2+}$:$Mg^{2+}$ selectivities are similar.

Of the six preferred dyes disclosed herein to exemplify the new indicators of the present invention, fura-2 will be the preferred dye for most applications although indo-1 is the prime candidate for flow cytometry. The stilbenes are marginally easier to synthesize but do not fluoresce as brightly as the others. In addition the stilbenes have complicated problems of photoisomerization and photodecomposition and are relatively difficult to load as acetoxymethyl esters (data not shown) due to insufficient solubility. It remains to be seen whether the slightly longer wavelengths of fura-3 can compensate for its lower brightness and less hydrophilic chromophore. The new dyes have already made $[Ca^{2+}]_i$ measurements possible in a number of previously intractable systems. The prospect of studying individual cells or aggregated tissue should enormously expand the range and ease of optical measurement of $[Ca^{2+}]_i$ and its ubiquitous messenger functions.

METHODS OF SYNTHESIS

Methods for synthesizing the new dyes disclosed herein include the following:

The present invention comprises a new class of fluorescent calcium-specific indicator dyes. Preferred examples of these new dyes include stil-1, stil-2, fura-1, fura-2, fura-3 and indo-1. FIGS. 1 and 2 outline the synthetic routes utilized in preparing these compounds. Full descriptions of the reaction conditions are described below. In both the figures and the discussion that follows, Roman numerals are used to identify the various chemical compounds.

The synthesis of the compounds claimed herein is described in the detailed synthesis of stil-1 (compound X), stil-2 (compound XIII), indo-1 (compound XXII), fura-1 (compound XXIX), fura-2 (compound XXXII), fura-3 (compound XXXV), and 5-formyl-quinl, ethyl ester, infra. Those skilled in the art will recognize that new forms of these dyes can be prepared by using related synthetic methods and starting materials.

To that end we point out that the key intermediate in the synthesis of compounds containing one fluorophore is the aldehyde shown below as compound 1a, or its analogues, including compounds VII and XXVI (see FIGS. 1 and 2; see also the discussion that follows):

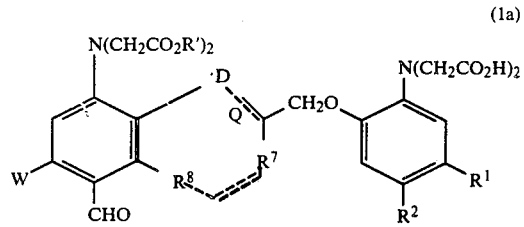

(1a)

During the formylation step, the presence of a methyl, halogen, or alkoxy group as radical $R^2$ prevents electrophilic substitution at that position, restricting formylation to the $R^1$-$R^2$-phenyl ring. Even if $R^2$ is hydrogen, a halogen at position $R^1$ will deactivate for electrophilic substitution the right hand benzene ring of the compound 1a, so that little or no formylation will occur on that ring. A methyl group at $R^1$ may slightly promote formylation at the $R^2$ position, but any doubly formylated impurities should be readily removable.

If $R^2$ is H and W is an O or $NR^5$ precursor, the ability of those W groups to promote electrophilic substitution is sufficient to direct formylation preferentially to the 5-position ortho to W. Since 8-aminoquinoline systems formylate much more readily than phenyl systems, no claimed combination of $R^1$ and $R^2$ will prevent the straightforward formylation of compounds containing quinoline or benzopyran systems.

If $R^2$ and W are both H, and $R^7$ and $R^8$ are not part of a closed ring, the 5-formyl compound, 1a, with $R^2$=H could be prepared by formylating with a limited amount of Vilsmeier reagent and separating the product from unchanged starting material and from doubly formylated product. Alternatively, the same 5-formyl compound could be prepared by using an acetal of 3-hydroxy-4-nitro benzaldehyde in place of compound III and 2-nitro-4-$R^1$-5-$R^2$-phenoxide in place of compound I and following the steps illustrated below for the preparation of compound VI (condensation with 1,2- dibromo-ethane, reduction, and alkylation with alkyl-bromoacetate). Mild acid hydrolysis of such an analogue of compound VI would unmask the aldehyde to give monoaldehyde, 1a.

The preparation of aldehydes with W=H, D=O. $R^7=R^8=H$, and various $R^1$ and $R^2$ substituents (see structure 1b, infra,) is based on starting with two appropriately substituted 2-nitrophenols. The potassium salt of each nitrophenol is prepared, then condensed sequentially with 1 equivalent of 1,2 dibromoethane. Reduction of the nitro groups, treatment with alkyl bromoacetate, and Vilsmeier formylation lead to the key aldehydes illustrated by compound 1b. One skilled in the art can readily modify the synthesis of compound VII, detailed below, to prepare such compounds.

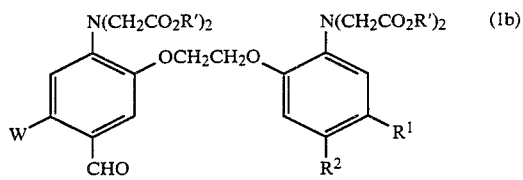

(1b)

Aldehydes 1b, which are derivatives of salicylaldehyde when W is OH, are synthesized in eight steps from p-hydroquinone. Key steps in the preparation of the salicylaldehyde include the acid-catalyzed, selective debenzylation (see reference 20) of the phenolic group ortho to the nitro in preference to the phenolic group meta to nitro. The resulting 2-nitro-4 benzyloxyphenol can then be used as a starting material in the procedure outlined above to prepare the key aldehyde, 1b. Attempts to convert XXIV to XXV by hydroxide displacement of benzyloxide were unsuccessful. The remaining benzyl protecting group survives hydrogenation with platinum catalysis (see reference 21) and Vilsmeier formylation but is finally removed by hydrogenation with palladium. Since the 4-benzyloxy substituent will accelerate the rate of formylation at the neighboring 5 position, no choice of $R^1$ and $R^2$ will interfere with monoformylation.

The preparation of aldehydes 1b where $W=NR^5H$ ($R^5=H$, Me, or Et) would begin with benzyloxycarbonyl protection of 4-($R^5$-amino)phenol. Nitration, nitrosation, or coupling with a suitable diazonium salt yields a substituted phenol analogous to compound XXI, infra. Such a phenol can be condensed with 1-bromo-2-(2-nitro-4-$R^1$-5-$R^2$-phenoxy)ethane, and reduced ($H_2$/Pt). Any of nitro, nitroso or diazonium salt groups will thereby be reduced to $NH_2$ without affecting the benzyloxycarbonyl groups. After alkylation with alkyl bromoacetate and formylation, the benzyloxycarbonyl group can be removed by hydrogenation with palladium on carbon to give an aldehyde 1b with $W=NR^5H$.

The preparation of the immediate precursors of aldehydes 1a, in which $R^7$ and $R^8$ are part of a quinoline ring, is described in reference 6. Starting with, for example, 2-methyl-6-W- 8-nitroquinoline, the 2-methyl group is iodinated to iodomethyl, then condensed with potassium 2-nitro-4-$R^1$-5-$R^2$-nitrophenoxide, reduced (Pt/$H_2$), and alkylated with methyl or ethyl bromoacetate (see reference 6). This compound can then be formylated to give aldehydes 1c.

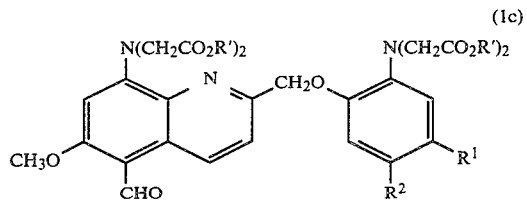

(1c)

This synthesis is illustrated below by the preparation of 5-formyl-quinl, ethyl ester (1c, where W=H, $R^1$=H, $R^2$=$CH_3$). One skilled in the art can use these teachings to prepare other compounds containing various groups $R^1$, $R^2$, $R^7$, and $R^8$.

The preparation of aldehydes 1a where $R^7$ and $R^8$ are part of a quinoline or benzopyran ring and W=OH begins, for example, with 2-methyl-6-methoxy-8-nitroquinoline. The methoxy group can be cleaved with $BBr_3$ or hot HI to yield a 6-hydroxy group, which can then be protected by reaction with dimethoxymethane under acid catalysis to yield 2-methyl-6-methoxymethyloxy-8-nitroquinoline. This can be used as starting material for the synthesis outlined above for aldehyde 1c, leading to compound 1c with $W=OCH_2OCH_3$. Mild acid hydrolysis of this compound gives aldehyde 1c with W=OH.

Aldehydes 1a where $R^7$ and $R^8$ are part of a quinoline or benzopyran ring and $W=NR^5$ could be prepared, for example, from 2-methyl-6-($R^5$-amino) quinoline by protecting the amine as benzyloxycarbonyl, and nitrating or nitrosating or coupling with a diazonium salt, then iodinating, condensing with 2-nitro-4-$R^1$-5-$R^2$-nitrophenoxide, reducing, and alkylating with alkylbromoacetate (see reference 6). Hydrogenation of such compound with palladium on carbon gives aldehydes 1c with $W=NR^5$.

The key intermediate in the synthesis of compounds containing two fluorophores is the dialdehyde shown below as compound 1d or its analogs.

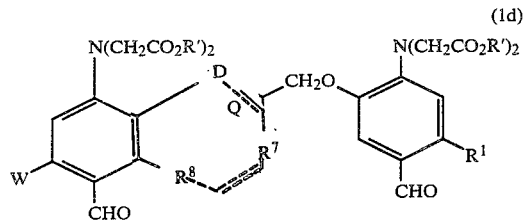

(1d)

By using a single or two different 2-nitrophenols with no 5 substituent and hydrogen, alkyl, or benzyloxy as a 4 substituent and following the synthesis outlined for aldehyde 1b, the Vilsmeier formylation step will produce the dialdehyde, 1d. This dialdehyde can then be condensed with any of the Wittig reagents used with 1a, leading to final compounds containing two long-wave fluorophores. To produce dialdehydes 1d where $R^7$ and $R^8$ are part of a quinoline ring system and, $R^2$=H and $R^1$=H, alkyl, or benzyloxy, the heterocycles formylate readily, so Vilsmeier formylation conditions suitable for formylating phenyl rings will give the desired dialdehyde.

Starting with the appropriate aldehyde, 1a or 1d, the synthesis of compounds with W=H proceeds by condensing the aldehyde with a Wittig reagent which consists of the $R^3$ and $R^{3a}$ substituted aromatic group, Z, as an $R^3$-$R^{3a}$-Z-methyl-triphenyl phosphorane. As an example, (4-ethoxycarbonyl)methyl-triphenyl phosphonium bromide, VIII, was condensed with aldehyde VII, leading ultimately to compound stil-1, IX. (See FIG. 1 and the synthesis of compounds VIII, VII and X that follows.) As a related example, (4-N,N-dimethylaminosulfonylphenyl)methyl triphenyl phosphonium bromide, XI, was condensed with aldehyde VII to ultimately produce compound stil-2, XII. Again see FIG. 1 and the synthesis of compounds XI, VII and XII that follows.

In analogous fashion, compounds can be prepared which contain a heterocyclic ring to lock the ethylene bridge in the trans configuration by connecting the ethylene to the rest of the dye portion of the molecule. ($Y'=Y=NR^5$). As an example, the synthesis of indo-1, XVII, is described, infra. The aldehyde of choice is condensed with a Wittig reagent carrying an ortho nitro group, which can then be reduced with triethyl phosphite to generate a nitrene, which cyclizes immediately to an indole (see reference 19).

Compounds can also be prepared which lock the ethylene bridge in the trans configuration by connecting the ethylene bridge to the chelating portion of the molecule. As an example, preparation of benzofuran derivatives in which W and X together are oxygen is illustrated infra by the synthesis of fura-1 (XXIX), fura-2 (XXXII), and fura-3 (XXXV). Beginning with aldehyde 1a with W=OH, the phenolic hydroxyl is remade into an ether with an electronegatively substituted arylmethyl group, which becomes Z in the final product. A base catalyzed Knoevenagel reaction then completes the benzofuran ring. Potassium fluoride on alumina is a particularly good catalyst for this condensation (see reference 22), perhaps because it has less tendency than other bases to attack the ester groups also present.

The analogous compounds containing an indole ring ($W=X=NR^5$) can be prepared from aldehydes 1a or 1d where $W=NHR^5$. The aldehyde is condensed with an appropriate halomethyl aromatic compound, for example, compounds such as XXVII, XXX or XXXIII (see FIG. 2). Ring closure with a base such as potassium fluoride on alumina leads to the desired indole, by analogy to XXVII, XXXI and XXXIV.

The groups $R^3$ and $R^{3a}$ are present when needed to provide hydrophilicity to the otherwise hydrophobic fluorophore "tail". $R^3$ and $R^{3a}$ will also modify somewhat the fluorescent properties of the long wave chromophore. One skilled in the art can readily prepare Wittig reagents or substituted arylmethyl compounds containing Z groups with appropriate precursor substituents so that the final compound will contain $R^3$ and/or $R^{3a}$=—$CO_2H$, —$CO_2R^4$, —$CONR^5R^6$, —$SO_3H$, —$SO_2NR^5R^6$, —$SO_2CF_3$, —$COCH_3$, or —CN, or $R^3$ and $R^{3a}$ together=—$(CO)NR^5(CO)$—. Other possible Z groups include heterocycles containing quaternary nitrogen, such as pyridinium. Z groups of this type do not require an $R^3$ or $R^{3a}$ substituent to reduce hydrophobicity of the fluorphore, although $R^3$ or $R^{3a}$ may still be useful to modify the fluorescence wavelength of the fluorophore. By way of example the syntheses of compounds containing $R^3$=—$CO_2H$ (stil—1, indo-1, fura-1, fura-2), —CN (fura-3), and —$SO_2NMe_2$ (stil-2) are shown below.

In these syntheses, the procedure for preparing the acetoxymethyl esters of the chelators was changed from earlier methods (see reference 23), which required preparation of the dry, solid, free acid form of the chelator and reaction with acetoxymethyl bromide in the presence of a hindered base, ethyldiisopropylamine. This procedure had given acceptable results with simpler BAPTA series chelators but proved erratic in yield and purity when applied to more complex derivatives such as the new dyes described here. One problem appeared to be that isolation of the chelators as dry solid free acids seemed to cause partial decomposition, perhaps by decarboxylation.

A more significant problem was found to be the purity of the acetoxymethyl bromide, heretofore prepared from acetyl bromide and paraformaldehyde and contaminated with a few mol % of bis(bromomethyl)ether as a nearly inseparable by-product (see reference 24). This ether seems to react faster with the carboxylic acid than the acetoxymethyl bromide does, yielding esters poorly hydrolyzable by cells. The percentage of such esters of course increases if a large excess of the crude bromide is used, and decreases if the bromide is partially purified by vacuum distillation through a spinning-band column. However, the best solution is to prepare acetoxymethyl bromide by an alternate route that generates no bis(bromoethyl)ether.

Prior to the present invention we knew that trimethylsilyl bromide would cleave esters to a free acid (TMS ester) plus the bromide of the esterifying group (see reference 39). However, until the present invention, we did not know that trimethylsilyl bromide could be used to effect cleavage of 1,1-bis acyloxyalkanes. Our problem was that when we tried to produce acetoxymethyl bromide using standard conditions for cleaving esters, we found that there was no reaction between trimethylsilyl bromide and methylene diacetate, even when heated overnight in a sealed tube at 110°. Much to our surprise we discovered that by adding about 10 mole % of a Lewis acid, the desired reaction was complete in 48 hrs. at room temperature. Also surprising was the lack of further interchange of bromide for acetoxy, which would have given dibromomethane. After distillation of acetoxymethyl bromide, no trace of bis(bromomethyl)ether could be detected in the product by NMR.

Likewise trifluoroacetoxymethyl bromide, $CF_3COOCH_2Br$, was prepared from methylene bis(trifluoroacetate), $CF_3COOCH_2OCOCF_3$; benzoyloxymethyl bromide, $C_6H_5COOCH_2Br$, was prepared from methylene dibenzoate, $C_6H_5COOCH_2OCOC_6H_5$; and 1-acetoxy-1-bromoacetone was prepared from 1,1-diacetoxyacetone, itself prepared by action of sodium acetate on 1,1-dichloracetone.

1-acetoxy-1-bromoacetone was extremely difficult or impossible to make by the standard preparation of 1-acyloxyalkyl bromide compounds, since the standard route would require preparation of pure anhydrous pyruvaldehyde, $CH_3COCHO$, to be reacted with acetyl bromide. Anhydrous pyruvaldehyde is extremely hygroscopic, unstable, and prone to polymerization. All the above preparations of 1-acyloxyalkyl halides carried out with trimethylsilyl bromide and a catalytic quantity of anhydrous zinc chloride at room temperature overnight; if the starting 1,1-diester was solid, a chlorinated solvent ($CH_2Cl_2$, $CHCl_3$, or $CCl_4$) was added to make a homogeneous reaction mixture. Products were characterized by boiling point, NMR, and halide titration. Different Lewis acids were tested in the case of methylene dibenzoate. $ZnCl_2$, $ZnI_2$, $ZrCl_4$, and $SnCl_4$ all proved effective, $AlCl_3$ less so. $BF_3.Et_2O$ and $Cu_2Br_2$ were ineffective. 1-acyloxyalkyl chlorides can also be obtained by this general procedure, though more vigorous conditions are required and lower yields result. Thus $C_6H_5COOCH_2OCOC_6H_5$ and $Me_3SiCl$ reacted in $CCl_4$ with $AlCl_3$ catalysis at 100° (sealed vessel) for 60 hrs. and gave a 35% yield of $C_6H_5COOCH_2Cl$.

Alpha-acyloxyalkyl bromides prepared by the above method are useful in preparing esters of the flourescent dyes disclosed and claimed herein. By way of example, acetoxymethyl esters of the compounds claimed herein were best made by: saponifying the methyl or ethyl esters of the target chelator (for example, compounds IX, XII, XVI, XXVIII, XXXI, or XXXIV, below and in FIGS. 1 and 2) with KOH, adding four to six equivalents of a tetrabutylammonium salt (preferably the hydroxide), and evaporating in vacuo to dryness. The residue was then extracted with dichloromethane, which dissolved the dyes as the tetrabutylammonium salts. This organic solution was dried thoroughly in vacuo, and the residue was taken up in dichloromethane, mixed with about 5-10 equivalents (per dye) of acetoxymethyl bromide (prepared according to the new method disclosed herein, see Method for Producing Acetoxymethyl Bromide, infra) and about 2 equivalents (per dye) of ethyl diisopropylamine, then stirred overnight. The solvent was then evaporated, the residue was taken up in benzene or toluene, washed with aqueous bicarbonate and water, dried and evaporated. The products were generally pure enough for use, but could be further purified on silica gel, if necessary.

Compound Synthesis

Most reagents and solvents used in the syntheses were ACS or HPLC grade, and used as received from Aldrich, Mallinckrodt, Fisher, or J. T. Baker. Dry dimethylformamide and dry pyridine were obtained from Aldrich, Gold Label, stored over 4A molecular sieves and used as received. $NaH_2PO_4$ from J. T. Baker was dried in an oven at 110°, then cooled in a vacuum desiccator. Dimethylamine was distilled from dimethylamine, hydrochloride, on NaOH pellets. Ethyl diazopyruvate was prepared from diazomethane and ethyl oxalyl chloride by standard methods. Potassium salts of 2-nitrophenoxides were prepared by adding a stoichiometric amount of concentrated aqueous KOH to the nitrophenol in methanol, then evaporating the solvent in vacuo until the stoichiometric weight was reached.

In testing the various reaction products, proton NMR spectra were recorded on Varian instruments at 60 MHz (EM-360), 80 MHz (CFT-20), 90 MHz (EM-390), and 100 MHz (HA-100). Peaks are reported below in the following format: NMR (solvent, operating frequency): chemical shift in ppm from tetramethylsilane, multiplicity (s=singlet, d=doublet, t=triplet, q=quartet, m=multiplet, br=broad), spin-spin coupling constant if appropriate, integrated number of protons. Sometimes several adjacent peaks are too close for their integrals to be separated, in which case only the total integral for a cluster is stated.

Compound I→II 1-bromo-2-(2'-nitro-5'-methylphenoxy)ethane (II) was prepared as follows:

57.6 g (0.30 mole) potassium 2-nitro-5-methylphenoxide (I), 187.4 g (1.0 mole) 1,2-dibromoethane, and 151 g dimethylformamide were heated together to 120°. The bright orange colour of the reaction mixture soon faded to pale yellow and a white precipitate was deposited. After cooling, the precipitate was filtered off and washed with water and dichloromethane. The insoluble residue was 1,2-bis(2-nitro-5-methylphenoxy)ethane, 5.87 g (0.018 mole). The combined organic phases of the filtrate were washed repeatedly with dilute NaOH until no more orange colour appeared in the extracts, then washed once with saturated aqueous NaCl containing a little $NaH_2PO_4$. After drying over $MgSO_4$, the organic phase was evaporated to dryness and the residue recrystallized either from petroleum ether (b.p. 60°-80°) or methanol-water. The yield of II was 34 g (44%), m.p. 44°-45°. NMR ($CDCl_3$, 60 MHz): 7.75, d, 8 Hz, 1H; 6.9-6.75, m, 2H; 4.36, t, 7 Hz, 2H; 3.6, t, 7 Hz, 2H; 2.36, s, 3H.

Compound II+III→IV 1-(2-nitrophenoxy)-2-(2'-nitro-5'-methylphenoxy) ethane (IV) was prepared as follows:

5.32 g (20.5 mmole) II and 3.98 g (22.5 mmole) potassium 2-nitrophenoxide (III) were stirred in 10 ml dimethylformamide and heated to 130° for 80 min. The mixture was cooled, diluted to 100 ml with water, and filtered; the precipitate was washed repeatedly with aqueous $Na_2CO_3$ and then water. After drying, it was recrystallized from 1.25 l boiling 95% ethanol containing 5 ml acetic acid, to which a little water was added after cooling. The yield of IV was 5.55 g, 85%, m.p. 150°-152°. NMR ($CDCl_3$, 80 MHz): 7.7-6.6, m, 7H; 4.34, s, 4H; 2.26, s, 3H.

Compound IV→V 1-(2-aminophenoxy)-2-(2'-amino-5'-methylphenoxy) ethane (V) was prepared as follows:

5.55 g IV were hydrogenated at room temperature and atmospheric pressure with 0.46 g palladium (5% on charcoal) catalyst in 95% ethanol. After full hydrogen uptake (13 hrs), the mixture was warmed, filtered while hot, decolorized with a pinch of $NaBH_4$, and chilled to −10°; the yield of V as white crystals was 4.03 g, 89%, m.p. 118°-119°. NMR ($CDCl_3$, 80 MHz): 6.8-6.5, m, 7H; 4.28, s, 4H; 3.5-3.7, br s, 4H; 2.24, s, 3H.

Compound V→VIa or VIb 1-(2-aminophenoxy)-2-(2'-amino-5'-methylphenoxy)ethane-N, N,N',N'-tetraacetic acid, tetraethyl ester (VIa) or tetramethyl ester (VIb) were prepared by either of two methods, as follows:

2.58 g (10 mmole) V, 11.3 g (53 mmole) 1,8-bis(dimethylamino)naphthalene, 0.79 g (5.3 mmole) sodium iodide, 8.91 g (53 mM) ethyl bromoacetate, and 9.5 g acetonitrile were stirred and refluxed under nitrogen for 18 hrs. The cooled mixture was diluted with toluene and filtered. The filtrate was extracted with phosphate buffer at pH2 until the 1,8-bis(dimethylamino)naphthalene was removed. The toluene solution was dried and evaporated and the residue recrystallized from 50 ml ethanol. The yield of the tetraethyl ester, VIa, was 5.27 g, 87%, m.p. 110°-110.5°. NMR ($CDCl_3$, 100 MHz): 6.88-6.6, m, 7H; 4.30, s, 4H; overlapping 4.18, s, 4.14, s, 4.08, q, 7 Hz, total 16H; 2.28, s, 3H; 1.18, t, 7 Hz, 12H.

In a larger-scale repetition, ethyl bromoacetate was replaced by methyl bromoacetate and 1,8-bis(dimethylamino)naphthalene was replaced by $Na_2HPO_4$, dried at 150°. Thus 25.83 g (100 mmole) V, 71 g (500 mmole) dried $Na_2HPO_4$, 5.9 g (39 mmole) NaI, 84.7 g (554 mmole) $BrCH_2CO_2Me$ and 104 g $CH_3CN$ refluxed under nitrogen with vigorous stirring by a crescent-shaped paddle for 18 hrs. The cooled reaction mixture was partitioned between water and toluene. The organic phase was evaporated to dryness and recrystallized from methanol. The yield of the tetramethyl ester, VIb, was 40.2 g (71%). After another crystallization from methanol, the m.p. was 95°–95.50°. NMR (CDCl$_3$, 90 MHz):6.83, s, 6.67, m, total 7H; 4.24, s, 4.13, s, 4.09, s, total 12H; 3.56, s, 3.54, s, total 12H; 2.23, s, 3H.

Compound VIb→VIIb 1-(2-amino-5-formylphenoxy)-2-(2'-amino-5'-methylphenoxy)ethane-N, N,N',N'-tetraacetic acid, tetramethyl ester (VIIb) was prepared as follows:

2.186 g (4.0 mmole) VIb was dissolved with stirring in 4.0 ml of dry dimethylformamide containing 0.4 ml of dry pyridine. The mixture was cooled in an ice-bath and phosphorus oxychloride (3.0 ml) was added dropwise. The reaction mixture turned black almost immediately. TLC (pet. ether - ethyl acetate 1:1) showed just a trace of product after 0.5 hr. The reaction mixture was stirred at 60° for 1 hr. and then left overnight at room temperature. The reaction mixture was dissolved in 50 ml CH$_2$Cl$_2$ and poured onto crushed ice mixed with aqueous NaOH. The aqueous layer was extracted with five 10 ml portions of CH$_2$Cl$_2$. The combined organic extracts were dried with MgSO$_4$, filtered and evaporated. The partially crystalline residue (1.75 g) was triturated with 5 ml isopropyl alcohol, filtered, washed with an ether - pet. ether mixture and dried. Yellowish crystals of VIIb were obtained, homogeneous on TLC and melting at 126°–7°, weight 1.50 g (65.3%). A second crop of crystals weighed 0.126 g, bringing the combined yield to 72%. Recrystallization from acetone-hexane gave pale yellow crystals, m.p. 131°–132°.

Compounds VIIb+VIII→IX 1-(2-amino-5-[(2-(4-ethoxycarbonylphenyl)-E-ethen-1-yl]-phenoxy)-2-(2'-amino-5'-methylphenoxy) ethane,N,N,N',N'-tetracetic acid, tetramethyl ester (IX) was prepared as follows:

574 mg (1 mmole) VIIb, 4-ethoxycarbonylbenzyltriphenylphosphonium bromide VIII (800 mg, 1.58 mmole), and 0.4 g anhydrous K$_2$CO$_3$ were stirred at 100° in 4 ml of dry dimethylformamide for 2.5 hrs. The cooled reaction mixture was partitioned between water and toluene, then the aqueous layer was extracted with more toluene. The residue after evaporating the solvent was chromatographed on silica in petroleum ether-ethyl acetate 9:1 (v/v). The mixture of stilbenes was isolated in 0.380 g (53%) yield. Four recrystallizations from ethylacetate-petroleum ether afforded pure transisomer of IX, m.p. 131°–132°. The isolation and purification steps were performed under dim orange safelight illumination. NMR (CDCl$_3$, 90 MHz): 7.99, d, 8 Hz, 2H; 8.48, d, 8 Hz, 2H; 7.1–6.85, m, 6.8–6.5, m, total 7–8H; 4.4–3.9, m, 14H; 3.58, s, 3.55, s, total 12H; 2.22, s, 3–4H; 1.37, t, 7 Hz, 3–5H.

The phosphonium salt (VIII) was prepared in 92% yield by reacting 12.16 g (50 mM) ethyl p-bromomethylbenzoate, XXVII (see reference 30), with 14.48 g (55 mM) triphenylphosphine in refluxing toluene overnight. The precipitate was filtered off from the cooled reaction mixture. After washing, and drying it had m.p. 241°–243° and weighed 23.3 g, 92% yield and was sufficiently pure for further use.

Although this compound contains mixed methyl and ethyl esters, it may be seen that use of appropriate esters of VIII and of VII will resolve this unimportant difference. The presence of mixed esters is not a problem as no shuffling of esterifying groups was seen, and the compound must be saponified before use as a chelating agent.

Compounds VII+XI→XII 1-(2-amino-5-[(2-(4-N,N-dimethylaminosulfonylphenyl)-E-ethen-1-yl] phenoxy)-2-(2'-amino5'-methylphenoxy)ethane-N,N,N',N'-tetraacetic acid, tetramethyl ester (XIII) was prepared as follows:

0.486 g (0.84 mmole) VIIb was refluxed overnight with 0.42 g (0.84 mmole) phosphonium salt XI and sodium methoxide (54 mg, 1 mmole) in CH$_2$Cl$_2$ overnight. The cooled reaction mixture was partitioned between water and chloroform. The crude product was chromatographed on silica in toluene-ethyl acetate 4:1 (v/v) and isolated as a thick syrup (112 mg, 17% yield). NMR (CDCl$_3$, 90 MHz): 7.65, d, 9 Hz, 2H; 7.4, d, 9 Hz, 2H; 7.3–7.0, m, integral obscured by toluene contamination; 6.9–6.5, m, 7H; 4.25, s, 4.20, s, 4.16, s, total 12H; 3.54, s, 12H; 2.77, s, 2.75, s, total 6H; 2.25, s, 3H.

Sulfonamide phosphonium salt XI was prepared analogously to VIII by reacting triphenylphosphine with N,N-dimethyl 4-(chloromethyl)benzenesulfonamide in refluxing toluene. Its m.p. was 275°–280°. The sulfonamide was prepared by reacting 4-chloromethyl benzenesulfonyl chloride (see reference 31) with a cold solution of dimethylamine in ether.

Compounds VIIb+XIV→XV 1-(2-amino-5-[2-(4-ethoxycarbonyl-2-nitrophenyl)-E-ethen-1-y-phenoxy), 2-(2'-amino-5'-methylphenoxy)ethane-N,N,N',N'-tetraacetic acid, tetramethyl ester (XV) was prepared as follows:

0.14 VIIb and 0.20 g XIV, and 0.6 g K$_2$CO$_3$ were stirred 3 hr. at 90° in 1 ml dry dimethylformamide. The reaction mixture was partitioned between toluene and water and the organic phase was evaporated and chromatographed on silica with toluene-ethyl acetate 6:1. The pooled fractions from the column were evaporated to a reddish oil, 135 mg, 69%.

Phosphonium salt XIV (m.p. 165–168) was prepared in 76% yield by reacting 1.5 g triphenylphosphine with 1.2 g ethyl 4-bromomethyl-3-nitrobenzoate in refluxing toluene overnight. The latter ester was prepared by stirring 2.43 g of ethyl p-bromomethylbenzoate, XXVII, in 10 ml concentrated H$_2$SO$_4$ at 5° C., while adding 1 ml conc HNO$_3$ (d 1.4) dropwise. The nitration mixture was poured onto crushed ice and extracted with CH$_2$Cl$_2$. The extract was washed with dilute NaOH, dried, and evaporated to give an oil which eventually crystallized, m.p. 41°–43°, yield 2.32 g, 80%. NMR (CCL$_4$, 90 MHz): 7.8, d, 9 Hz, 7.67, d. 2 Hz, 7.58, dd, 9 Hz+2 Hz, total 3H; 4.45, s, 2H; 3.9, s, 3–4H.

Compound XV→XVI 1-(2-amino-5-[6-ethoxycarbonylindolyl-2-]phenoxy),2-(2'-amino-5'-methylphenoxy)ethane-N,N,N',N'-tetraacetic acid, tetramethyl ester (XVI) was prepared as follows:

300 mg (0.392 mmole) XV were dissolved in 2 ml triethyl phosphite and refluxed overnight under nitrogen. The reaction mixture was evaporated to dryness in vacuo and the residue was chromatographed on silica in toluene-ethyl acetate 4:1. The cyclized product XVI was obtained as a dark oil (160 mg, 55.6%) which crystallized after drying at 0.1 torr. Recrystallization from methanol produced crystals melting at 96°–97°. NMR (CDCl$_3$, 90 MHz): 8.08, s, 1H; 7.73, d, 8 Hz, 7.5, d, 8 Hz, total 2H; 7.21, m, 2H; 6.9–6.5, m, 5H; 4.35, g, 7 Hz, 4.21, s, 4.14, s, 4.09, s, total 12–14H; 3.58, s, 3.54, s, 11–12H; 2.17, s, 3H; 1.8, br s, about 2H (may contain H$_2$O peak); 1.33, t, 7 Hz, 3H.

Compound XVIII→XIX 1,4-di(benzyloxy)benzene (XIX) was prepared as follows:

To a stirred suspension of 55 g (0.5 mole) hydroquinone (XVIII) and 143.1 g (1.1 mole) benzyl chloride in 100 ml ethanol was added a solution of 60.2 g (0.91 mole) potassium hydroxide in ethanol. After 1 hr, the mixture was poured into water. The precipitate was filtered off several hours later, dried at 70°, and recrystallized from 3.5 liters of boiling ethanol. The yield of XIX was 105 g, 73%, m.p. 128°–130° (literature values (32) range from 126.5° to 130°). NMR (CDCl$_3$, 100 MHz): 7.35, s, 10H; 6.87, s, 4H; 4.98, s, 4H.

Compound XIX→XX 2-nitro-1,4-di(benzyloxy)benzene (XX) was prepared as follows:

18.3 g (0.203 mole) 70% aqueous nitric acid were diluted to 50 ml with glacial acetic acid and added to a suspension of 58 g (0.200 mole) XIX in 200 ml acetic acid. The mixture was stirred and gently warmed to 50°, whereupon the starting material dissolved and product began to crystallize out. After cooling the mixture and filtering off a first crop, water was added dropwise to precipitate a second crop. The total yield of XX was 65.6 g, 98%, m.p. 81°–82.5° (83° was reported in ref. 33). NMR (CDCL$_3$, 100 MHz): 7.5–6.9, M, 13H; 5.15, s, 5.03, s, total 4H.

Compound XX→XXI 2-nitro-4-benzyloxyphenol (XXI) was prepared as follows:

A solution of 50.4 g (0.15 mole) XX in 100 ml ethanol-free chloroform was treated with 15.0 ml (0.2 mole) trifluoroacetic acid and kept at room temperature for 48 hours, at which time an NMR spectrum showed ca. 90% conversion of the starting material, as judged by the amplitude of the peak at =4.92. The excess acid was neutralized with 5M aqueous potassium hydroxide. The organic phase was repeatedly extracted with dilute aqueous potassium carbonate until the aqueous layer was pale orange instead of dark brown as at first. The chloroform solution was then diluted with 1.5 volumes of diethyl ether and treated with 60 ml 5M potassium hydroxide. The dark red precipitate of potassium 4-benzyloxy-2-nitrophenoxide was filtered off, acidified with dilute HCl, and extracted with six 600 ml portions of petroleum ether (b.p. 60°–80°). After combining the extracts and evaporating the petroleum ether, the residue was recrystallized from boiling methanol to which water was added dropwise after cooling. The yield of XXI was 31–32 g, 84–87%, m.p. 67°–70°.

NMR (CCl$_4$, 100 MHz): 10.24, s, 1H; 7.52, d, 3 Hz, 1H; 7.32, s, 5H; 7.19, dd, 3 Hz, and 9Hz, 1H; 7.00, d, J=9 Hz, 1H; 5.01, s, 2H.

Compounds XXI+II→XXII 1-(2-nitro-4-benzyloxyphenoxy)-2-(2'-nitro-5'-methylphenoxy)ethane (XXII) was prepared as follows:

A mixture of 2.45 g (10 mmole) XXI, 2.8 g (108 mmole) II, 0.76 g (5.5 mM) anhydrous K$_2$CO$_3$, and 5 ml dimethylformamide was heated to 150° and stirred for 15 min. While still fairly warm, the stirred mixture was treated dropwise with water until the initial deposit of KBr dissolved and the product began to crystallize. It was filtered off, dried (crude yield 90%), and recrystallized by dissolving in a minimum quantity of hot acetone and precipitating with twice its volume of petroleum ether. The light yellow crystals of XXII had m.p. 143°–144°.

Compound XXII→XXIII 1-(2-amino-4-benzyloxyphenoxy)-2-(2'-amino-5'-methylphenoxy)ethane (XXIII) was prepared as follows:

5 g (11.8 mmole) XXII and 0.5 g of 5% platinum on charcoal were suspended in 100 ml absolute ethanol and stirred under hydrogen. The theoretical volume was taken up in 5 hrs. but the mixture was left under hydrogen overnight, after which the cumulative uptake was 19% higher than theoretical. Another 5 g of XXII added to the same hydrogenation mixture also took up the same higher-than-theoretical amount of hydrogen overnight. The product XXIII was recrystallized from acetone and had melting point 129°–132°. The NMR spectrum showed that the benzyl groups had not been lost. (CDCl$_3$+CD$_3$SOCD$_3$, 90MHz): 7.29, s, 5H; 6.75–6.45, m, 4H; 6.32, d, 3 Hz, 1H; 6.12, dd, 3 Hz+7 Hz, 1H; 4.93, s, 2H; 4.3, br s, 4.26, s, total 4H; 2.27, s, 3H.

Compound XXIII→XXIV 1-(2-amino-4-benzyloxyphenoxy)-2-(2'-amino-5'-methylphenoxy)ethane-N,N,N',N'-tetracetic acid, tetraethyl ester (XXIV) was prepared as follows:

3.64 g (10 mmole) XXIII, 10.72 g (50 mmole) 1,8-bis(-dimethylamino)naphthalene, 2.0 g (13 mmole) dried NaI, 8.35 g (50 mmole) ethyl bromoacetate, and 15 ml acetonitrile were stirred and refluxed under nitrogen for 40 hrs, with a further addition of 1.5 ml ethyl bromoacetate and 2 g 1,8-bis(dimethylamino)naphthalene after the first 24 hrs. The cooled reaction mixture was evaporated to dryness, diluted with toluene and filtered; the gray precipitate was washed repeatedly with further small portions of toluene. The pooled toluene solutions were repeatedly extracted with phosphate buffer until the washings were pH 2, the same as the fresh buffer. The toluene solution was then washed with water and dried over MgSO$_4$. After evaporation of the toluene under reduced pressure, the residue was washed with petroleum ether-ethyl acetate 9:1 v/v to remove traces of ethyl bromoacetate. The yield of XXIV was 6.4 g (90%), m.p. 95°–96°.

Compound XXIV→XXV 1-(2-amino-4-benzyloxy-5-formylphenoxy)-2-(2'-amino-5'-methylphenoxy)ethane-N,N,N',N'-tetraacetic acid, tetraethyl ester (XXV) was prepared as follows:

0.35 g (0.5 mmole) XXIV was dissolved in 2 ml of dry dimethylformamide and 0.4 ml pyridine. POCl$_3$ (0.4 ml, 4 mmole) was added at 0°. After 0.5 hr., the reaction mixture was allowed to warm up and left overnight at room temperature. The reaction mixture was neutralized with ice-cold aqueous NaOH and extracted with three 20 ml portions of toluene. Evaporation of the toluene phases gave crystalline XXV, m.p. 114°–115° (256 mg, 73% yield). NMR (CDCl$_3$, 90 MHz): 10.33, s, 1H; 7.35, s, 5–7H; 6.8–6.6, m, 4H; 6.3, s, 1H; 5.08, s, 2H; 4.25–3.9, m, 20H; 2.21, s, 3–4H; 1.14, t, 7Hz, 12–14H.

Compound XXV→XXVI 1-(2-amino-4-hydroxy-5-formylphenoxy)-2-(2'-amino-5'-methylphenoxy)ethane-N,N,N',N'-tetraacetic acid, tetraethyl ester (XXV) was prepared as follows:

XXV was debenzylated by hydrogenation in glacial acetic acid with 5% Pd on charcoal catalyst at atmospheric pressure. XXVI had m.p. 109°–111°.

Compounds XXVI+XXVII→XXVIII 1-(2-(4-ethoxycarbonylphenyl)-6-aminobenzofuran-5-oxy)-2-(2'-amino-5'methylphenoxy)ethane-N,N,N',N'-tetraacetic acid, tetraethyl ester (XXVIII) was prepared as follows:

Although a low yield of impure XXVIII can be obtained directly by heating XXVI and XXVII in DMF at 100° for 70 hr., it is better to do the esterification and furan ring closure in separate steps. 65 mg XXVI (0.1 mmole), 50 mg ethyl 4-bromomethylbenzoate (XXVII), 0.2 g $K_2CO_3$, and 10 mg tetrabutylammonium hydrogen sulfate were stirred overnight under reflux in acetonitrile. The product, the 4-ethoxycarbonylbenzyl ether of XXVI, was isolated by preparative layer chromatography with petroleum ether-ethyl acetate 1:1, giving 57 mg, 71% yield, m.p. 109°–110°. NMR ($CDCl_3$, 90 MHz) 10.34, s, 1H; 8.06, d, 8 Hz, 2H; 7.47, d, 8 Hz, 2H; 7.3, s, partly obscured by $CHCl_3$; m, 6.8–6.55, 3H; 6.3, s, 1H; 5.16, s, 2H; 4.37, q, 7 Hz, 4.21, s, 4.14, s, 4.05, q, 7 Hz, 4.02, q, 7 Hz, total 22H; 2.23, s, 3H; 1.38, t, 7 Hz, 1.17, t, 7 Hz, 1.15, t, 7 Hz, total 15H. 39 mg of this ether (0.05 mmole) was stirred with potassium fluoride/alumina reagent (see reference 22) in 1 ml dimethylformamide for 2 hrs. at 150°. The fluorescent product was isolated in 21 mg (54%) yield by preparative layer chromatography on silica with toluene-ethyl acetate 1:1. More prolonged reaction times in DMF lead to increasing ester hydrolysis. NMR ($CDCl_3$, 90 MHz): 8.15, d, 9 Hz, 7.89, d, 9 Hz, total 4–5H; 7.15–7.05, m, 6.78, m, total 6–7H; m, 3.9–4.5, 20–22H; 2.23, s, 3H; 1.0–1.4, m, 13–17H.

Compounds XXVI+XXX→XXXI 1-(2-(5-ethoxycarbonyloxazol-2-yl)-6-aminobenzofuran-5-oxy)-2-(2'-amino-5'-methylphenoxy)ethane-N,N,N',N'-tetraacetic acid, tetraethyl ester (XXXI) was prepared as follows:

In this case, ether formation and furan ring closure can be done in one step. 0.5 (g) (0.77 mmole) XXVI, 0.2 g ethyl 2-chloromethyloxazole-5-carboxylate (XXX), and 0.5 g $K_2CO_3$ were stirred in 2 ml dry dimethylformamide at 100° for 1.5 hr. The reaction mixture was cooled, diluted with water, acidified with HCl and extracted with $CHCl_3$. The combined extracts were dried with $MgSO_4$ and evaporated to a dark, semicrystalline residue. Filtration through a short column of silica gel washed with 1:1 toluene-ethyl acetate gave, after evaporation, yellow crystals, which after titration with hexane-ethyl acetate 9:1 and filtration, melt sharply at 138°. The yield was 420 mg, 68%. NMR ($CDCl_3$, 90 MHz): 8.11, s, 1H; 7.69, s, 1H; 7.34, s, 7.29, s, total 2H; 6.97–6.87, m, 3H; 4.57, q, 7 Hz, 4.45, s, 4.35, s, 4.25, s, 4.35, s, 4.25, s, 4.18, q, 7 Hz, 4.22, q, 7 Hz, total 22H; 2.31, s, 3H; 1.44, t, 7 Hz, 3H; 1.21, t, 7 Hz, 1.19, t, 7 Hz, total 12H. Ethyl 2-chloromethyloxazole-5-carboxylate (XXX) was prepared by reacting chloracetonitrile with ethyl diazopyruvate in analogy to the synthesis (see reference 34) of ethyl 2-methyloxazole-5-carboxylate. Ethyl diazopyruvate, 0.1 g, a few mg of cupric acetylacetonate, and 0.4 ml of chloracetonitrile were kept overnight at 60° in benzene solution. The cooled reaction mixture was partitioned between aqueous $NaHCO_3$ and ether. The organic layer was dried, evaporated, and chromatographed on silica, eluting with petroleum ether-ethyl acetate 9:1 v/v. The product isolated was further purified by bulb-to-bulb distillation at 12 torr, 90° air bath temperature. Though the NMR spectrum still showed significant impurities, GC-MS analysis showed that by far the dominant fraction had the correct parent M/e=189 and isotopic pattern expected for XXX, with fragments at 161 (—$C_2H_4$ or —CO), 154 (—Cl), 144 (—$OC_2H_5$), and a base peak at 116 (—$COOC_2H_5$).

Compounds XXVI+XXXIII→XXXIV 1-(2-(4-cyanophenyl)-6-amino-benzofuranoxy-5-)-2-(2'-amino-5'-methylphenoxy)ethane-N,N,N',N'-tetraacetic acid, tetraethyl ester (XXXIV) was prepared as follows:

140 mg (0.22 mmole) XXVI, 88 mg (10.58 mmole) p-cyanobenzyl chloride (XXXIII), 350 mg $K_2CO_3$, and 30 mg tetrabutylammonium hydrogen sulfate were stirred in 3 ml dimethylformamide for 4 hrs. at 125°. The dark reaction mixture was diluted with water and extracted into toluene. The evaporated toluene phase was chromatographed on silica with a toluene-ethyl acetate mixture. A fast-running fluorescent band was discarded; the subsequent main peak was evaporated to give 82 mg oil, which crystallized. Further recrystallization from petroleum ether-ethyl acetate gave a m.p. of 120°–121°, though a better solvent could probably be found. The yield was 51%. The NMR was crudely as expected, but not precisely assignable. NMR ($CDCl_3$, 90 MHz): 7.9–7.1, m, 7.03, m, 6.70, m, 4.1–4.3, m, 22S, s, 0.8–1.4, m.

Preparation of Free Acids

Method for Synthesizing Acetoxymethyl Bromide

The solid free acids are not stable for more than a few days, though their fully ionized salts are considerably more stable. The final products were not characterized by NMR, but were carefully studied by UV, fluorescence, and $Ca^{2+}$ titration (see Table 1). The $Ca^{2+}$ titration showed that no preparation contained more than 10% di- or tricarboxylate compounds (data not shown).

Coumpound IX→X 1-(2-amino-5-[(2-(4-carboxyphenyl)-E-ethenyl-1]-phenoxy)-2-(2'-amino-5'-methylphenoxy)-ethane-N,N,N',N'-tetracetic acid (X) was prepared by saponification of IX.

Compound XII→XIII 1-(2-amino-5-[(2-(4-N,N-dimethylaminosulfonyl-phenyl)-E-ethenyl-1-]phenoxy-)-2-(2'-amino-5'-methylphenoxy)ethane-N,N,N',N'-tetraacetic acid (XIII) was prepared by saponification of XII.

Compound XVI→XVII 1-(2-amino-5-[6-carboxyindolyl-2-]phenoxy)-2-(2'-amino-5'-methylphenoxy-)ethane-N,N,N',N'-tetraacetic acid, tetramethyl ester (XVII) was prepared by saponification of XVI.

Compound XXVII→XXIX 1-(2-(4-carboxyphenyl)-6-amino-benzofuranoxy-5-)-2-(2'-amino-5'-methylphenoxy)-ethane-N,N,N',N'-tetraacetic acid (XXVIII) was prepared by saponification of XXVII.

Compound XXXI→XXXII 1-(2-(5'-carboxyoxazol-2'-yl)-6-amino-benzofuranoxy-5-)-2-(2'-amino-5'-methylphenoxy)ethane-N,N,N',N'-tetraacetic acid (XXXII) was prepared by saponification of XXXI.

Compound XXXIV→XXXV 1-(2-(4-cyanophenyl)-6-amino-benzofuranoxy-5-)-2-(2'-amino-5'-methylphenoxy)ethane-N,N,N',N'tetraacetic acid (XXXV) was prepared by saponification of XXXIV.

Saponification to free acids

In the synthetic reactions ethyl or methyl esters are saponified to free chelator polyanions by dissolving the ester in a water-miscible solvent such as methanol, ethanol, or dioxane and adding excess aqueous sodium, potassium, or tetrabutylammonium hydroxide. We found that sometimes brief warming was helpful to start the hydrolysis of esters that precipitate upon addition of aqueous solutions. However, as long as the chelator had been in homogeneous solution containing at least 0.1 M excess NaOH or KOH for a few hours, hydrolysis was complete as judged by thin layer chromatography on silica with butanol-acetic acid-water 4:1:1 or 4:1:5 v/v, or by $Ca^{2+}$ titration. Tetrabutylammonium hydroxide seemed to be slower, perhaps because the cation was less able than $K^+$ or $Na^+$ to pair with and partially neutralize the charge of intermediate stages of hydrolysis, so that electrostatic repulsion of hydroxide slowed further hydrolysis.

Quinl, tetraethyl ester

The synthesis of quinl/Et, 2-([2-(bis[ethoxycarbonyl)methyl]amino)-5-methylphenoxy]methyl)-8-(bis[(ethoxycarbonyl)methyl]amino)quinoline is described in reference 6.

5-formyl-quinl, tetraethyl ester 2-([2-(bis[(ethoxycarbonyl)methyl]amino)-5-methylphenoxy]methyl)-5-formyl-quinoline-8-(bis[(ethoxycarbonyl)methyl]amino), 2a, was prepared as follows:

64.1 mg quinl/Et (103 micromole) was added to a mixture of 42.3 mg $POCl_3$ (276 micromole) and 50 microliters dimethylformamide at 0°. 50 microliters more DMF was then used to rinse the quinl/Et powder down the sides of the flask. Eventually a clear dark orange syrup was formed and was left for 2 hrs. at room temperature, at which time thin layer chromatography (silica, 49:1 v/v chloroform-methanol) showed that reaction was complete. The reaction mixture was diluted with water and washed with toluene. The aqueous phase was partly neutralized with $NaHCO_3$ to pH2 and re-extracted with toluene. The pooled toluene phases were washed once with aq. $NaHCO_3$, then dried over $Na_2SO_4$ overnight. Evaporation of the toluene left a yellow orange gum, 63.4 mg; trituration of this with di-isopropyl ether initially dissolved the gum, but soon a very pale yellow powder crystallized out. When filtered off and dried, the crystals of 2a weighed 43.8 mg, 67 micromole, 65% yield.

NMR (80 MHz, $CDCl_3+CCl_4$): 9.96, s, 1H; 9.61, d, 1H, 9 Hz; 7.75, d, 9 Hz, 7.71, d, 8 Hz, total 2H; 6.8–6.6, m, 4H; 5.12, s, 2H; 4.45, s, 4.23, q, 7 Hz, 4.08, s, 4.03, q, 7 Hz, total 16H; 2.14, s, 3H; 1.24, t, 7 Hz, 1.13, t, 7 Hz, total 12H.

Method for Producing Acetoxymethyl bromide

Acetoxymethyl bromide, $CH_3COOCH_2Br$, was prepared by stirring 4.0 g (30 mM) methylene diacetate and 5.0 g (33 mM) trimethylsilyl bromide, in the presence of 60 mg anhydrous $ZnCl_2$ but no added solvent, for 48 hr at room temperature. The product was distilled crudely at 10 torr, 40°–60° then refractionated through a Vigreaux column at 10 torr, 55°–57°, yielding 4.04 g, 87%, containing no detectable $BrCH_2OCH_2Br$ by NMR. Lewis acid catalysis is essential; without it there is no reaction even at 110° in a sealed tube overnight. Methylene diacetate was prepared from paraformaldehyde and acetic anhydride (see reference 35) and was carefully distilled to remove $CH_3COOCH_2OCH_2OCOCH_3$.

EXPERIMENTAL PROCEDURES

Experimental procedures used in synthesizing or testing the new dyes include the following:

UV absorbance spectra were recorded on a Cary 210 spectrophotometer at 22°±2° C. Fluorescence spectra were recorded either on a Perkin-Elmer MPF-44A spectrofluorometer or on a Spex Fluorolog 111, both in ratio mode with Rhodamine B quantum counters. Correction factors for the emission monochromator and photomultiplier were obtained by comparing the spectra of reference compounds with their known quantum distributions (see reference 9). The quantum yields were determined by comparing the integral of the corrected emission spectrum of the test sample with that of a solution of quinine bisulfate in 1N sulfuric acid. The concentration of quinine was adjusted to give the same absorbance as the sample at the exciting wavelength. The quantum efficiency of quinine was taken to be 0.55 (see reference 10).

Calcium and magnesium affinities of EGTA at high ionic strength were measured by titrating 125 micromole portions of EGTA (Fluka Chemical, puriss grade) with 1.00M KOH (J.T. Baker, low in carbonate). The EGTA was dissolved in 25 ml medium containing 225 mM KCl, 25 mM NaCl, and in some runs 10 mM $CaCl_2$ or 21 mM $MgCl_2$. This solution was stirred in a Radiometer TTA80 Titrator, bubbled continuously with nitrogen, and thermostatted at 18° C. while KOH was added in 0.005 or 0.01 ml aliquots from a ABU80autoburet. The pH was measured with a PHM84 meter, a G2040C electrode and an Ag/AgCl reference electrode connected to the titration solution by a long length of 0.01 inch catheter tubing filled with 3M KCl; this electrode chain was calibrated with phthalate (4.001), phosphate (6.889), and borax (9.245) buffers made according to National Bureau of Standards recipes. The fifty to eighty pH readings in each titration were analyzed by the FORTRAN program SCOGS of Sayce (see reference 36). The resulting proton ionization constants for EGTA were 9.537 and 8.961 with computed uncertainties of ±0.012 and ±0.008 respectively. These $pK_a$ values are "mixed" constants, i.e. $a_{H+}[EGTA^{4-}]/[H.EGTA^{3-}] = 10^{-9.54}M$ where $a_{H+} = 10^{-ph}$. The log absolute stability constants for Ca.EGTA and Mg.EGTA were calculated to be 10.777±0.011 and 4.567±0.021; the proton $pK_a$'s for Ca.EGTA and Mg.EGTA came out at 3.51±0.49 and 7.885±0.05 respectively. At this ionic strength and any pH>4, the effective stability constant $K'_{Ca}$ may be calculated as (antilog 10.77)·[1 +antilog (3.51−pH)]/[1+antilog (9.537−pH)+antilog (9.537+8.961−2·pH)]in units of liters/mole. Analogously $K'_{Mg}$=(antilog 4.567)·[1+antilog (7.885−pH)]/[1+antilog (9.537−pH)+antilog (9.537+8.961−2·pH)].

Free [$Ca^{2+}$] levels were controlled by Ca-EGTA buffers assuming apparent dissociation constants for Ca-EGTA of 380 nM at pH 7.00 in 0.1M KCl, 20° C.; 151 nM at pH 7.20 in 0.1M KCl, 20° C.; 214 nM at pH 7.05 in 130 mM KCl, 20 mM NaCl at 37° C.; and 490 nM at pH 7.02 in 225 mM KCl, 25 mM NaCl at 18° C. The first three apparent dissociation constants were calculated from the tables of Martell & Smith (see reference 11) as discussed in referencess 1 and 12. The last value was freshly determined in this study because no appropriate absolute constants were available at the higher ionic strength, and existing estimates in the biological literature (see references 13-17) vary by an unacceptably large range, >0.5 log unit. For this determination we chose the classic and reliable method of pH titration in the presence and absence of excess metal ion (see references 18). Details are included in the METHODS OF SYNTHESIS section, supra.

Free [$Mg^{2+}$] was likewise controlled by Mg-EGTA buffers assuming an apparent dissociation constant for Mg-EGTA of 21 mM at pH 7.18 in 130 mM KCl at 20°, 8.96 mM at pH 7.05 in 130 mM KCl, 20 mM NaCl at 37°, and 99 mM at pH 7.02 in 225 mM KCl, 25 mM NaCl at 18°. Again, the last value was freshly determined in this study.

Heavy metal binding constants were measured as follows. Affinities of stil-1 and fura-2 for $Zn^{2+}$ were measured by titrating 1-2 microM dye in 120 mM KCl, 5 mM $K_2H_2$EGTA, 10 mM MOPS, 5 mM Tris, with 1M $ZnCl_2$ dispensed from a micrometer syringe. At each stage of the titration (13 steps from 0 to 7 mM total $ZnCl_2$ added) the pH was adjusted with base to be within 0.02 units of 7.12, the actual pH values was noted for computation of pZn, and the excitation spectrum was recorded at room temperature. The family of spectra had a roughly similar appearance to FIG. 3 and was likewise analyzed by Hill plots of the fluorescence at 340 and 380 nm, i.e., by plotting log [(F−$F_{min}$)/(-$F_{max}$−F)] vs. log [free $Zn^{2+}$] where $F_{min}$ and $F_{max}$ are the fluorescences at zero and excess $Zn^{2+}$ respectively. For computation of free $Zn^{2+}$, the effective dissociation constant of EGTA for $Zn^{2+}$ was taken to be 4.27 nM at pH 7.11 and to decrease by 0.02 log unit per 0.01 increase in pH. (see reference 11).

Since $Mn^{2+}$ and $Fe^{2+}$ quench fura-2, the affinities for these ions relative to $Ca^{2+}$ could be assessed by direct competition between the metal ions each in stoichiometric excess. This method, similar to that of Hesketh, et al. (see reference 26), does not involve EGTA or other buffers. Fluorescences of 0.5 microM fura-2 at room temperature were recorded in solutions containing 100 mM KCl, 10 mM KMOPS, pH 7.2. One series also contained 0, 0.1, or 1 mM $MnSO_4$ and 0, 1.1, 2.2, 4.4, or 8.8 mM $CaCl_2$; another series had 2 mM $CaCl_2$ and 0, 0.1, 0.2, 0.5, 1, 2 mM Fe($NH_4$)$_2$($SO_4$)$_2$; and a third series with 0.2 mM Fe($NH_4$)$_2$($SO_4$)$_2$ and 0, 0.2, 0.4, 0.8, 2, 4, and 8 mM $CaCl_2$. Measurements with Fe(II) were made in a cuvet sealed by a septum and continually bubbled with nitrogen; the solutions stayed clear and nearly colorless until the septum was removed after the end of the experiment, whereupon deposition of yellow Fe(OH)$_3$ followed rapidly.

Binding to membranes was assessed by adding 0.3 ml portions of well-washed, packed human red cells to 1.5 ml volumes of 2 microM fura-2, fura-3, or indo-1, in media containing 145 mM NaCl, 5 mM KCl, 10 mM MOPS, 1 mM $Na_2HPO_4$, 1 mM $MgCl_2$, and either 1 mM EGTA or 1 mM $CaCl_2$. After several minutes equilibration, the suspensions were centrifuged and the fluorescence of the supernatant was measured with front-face geometry. The slight loss in fluorescence from its level before equilibration with red cells was taken to be an upper limit on the dye binding to membranes since dilution by residual extracellular water in the packed red cells or inner filter effects from traces of leaked hemoglobin would also have tended to depress the fluorescence.

EXAMPLES

Specific properties and embodiments of the present invention are outlined in the following examples. Such examples are for illustrative purposes only and are not intended to limit the scope of the claims in any way.

EXAMPLE I

Absorbance spectra

Absorbance and fluorescence properties for the new indicators disclosed herein, as exemplified by stil-1, stil-2, indo-1, fura-1, fura-2 and fura-3, in the presence and absence of $Ca^{2+}$, are shown in Table I, supra. As the data in the table illustrates, the absorbance spectra for the new indicators are within the range expected for stilbene chromophores. Absorbance maxima are in the near UV, with extinction coefficients in the range $2-3\times10^4 M^{-1}$ $cm^{-1}$. The data in Table I also shows that binding of $Ca^{2+}$ shifts all the absorbance spectra to shorter wavelengths.

EXAMPLE II

Fluorescence properties

The fluorescence excitation spectra for the new indicators disclosed herein shift to shorter wavelengths as [$Ca^{2+}$] increases, much as the absorption spectra do. An example is shown in FIG. 3, which presents a set of excitation spectra for fura-2 in calibration buffers of varied [$Ca^{2+}$]. Given such calibration data, the [$Ca^{2+}$] in an unknown solution containing the dye can be deduced from the shape of the excitation spectra. An explicit formula for this calibration is derived in Example VII. In contrast to the fluorescence excitation spectra, there is a large variation among the indicators when it comes to emission wavelength shift. Although all the compounds show some shift, only those of the indole-type (as exemplified by indo-1) show significant shifts.

Since the stilbene-type (as exemplified by stil-1 and stil-2) and benzofuran-type (as exemplified by fura-1, fura-2 and fura-3) indicators change their emission wavelengths very little upon binding $Ca^{2+}$, their families of emission spectra at different [$Ca^{2+}$] do not show any point where all the curves cross each other. This is not the case for the indole-type indicators since their $Ca^{2+}$-complexes have a much shorter emission wavelength than do their $Ca^{2+}$-free species. Consequently, indole-type emission spectra, as exemplified by indo-1, show a clear crossover point whose position depends on the excitation wavelength because that affects the relative efficiency with which $Ca^{2+}$-free and $Ca^{2+}$-bound forms are excited. This is illustrated in FIG. 4. That figure also shows that an excitation wavelength of 355-356 nm (as would be produced by a krypton laser), indo-1 gives the family of emission spectra in which the long and short wavelength peaks are of comparable amplitude.

The quantum yields of fluorescence for all the new indicators are quite respectable, ranging up to ca. 0.5 for indo-1 and fura-2 with $Ca^{2+}$. In all cases the $Ca^{2+}$-complex has a quantum efficiency between 1.3 and 2.1-fold higher than the $Ca^{2+}$-free dye. For comparison, the quantum efficiencies of quin2 with and without $Ca^{2+}$ are 0.14 and 0.029 respectively (see reference 6). Since fura-2 at half-saturation has a quantum efficiency four to five times higher than quin2 at half-saturation, and fura-2 has extinction coefficients about six times higher than quin2, one would predict that fura-2 should be some thirty-fold brighter than quin2. This estimate is confirmed by FIG. 5, which shows that the fluorescence of 1 microM fura-2 at high and low $Ca^{2+}$ is bracketed by that of 30 microM quin2 under identical conditions.

EXAMPLE III

$Ca^{2+}$-binding constants

Dissociation constants for the new indicators disclosed herein, as exemplified by chelators stil-1, stil-2, indo-1, fura-1, fura-2 and fura-3 (see Table I, infra), are in the range 100–300 nM at ionic strengths near 0.1 to 0.15. Such values are close to the dissociation constant (110 nM) of the parent compound BAPTA (see reference 6), showing that the substituents that make up the rest of the chromophores are only slightly electron-withdrawing. Fura-2 was also examined at higher ionic strengths, ca. 250 mM (225 mM KCl, 25 mM NaCl). A considerable decrease in $Ca^{2+}$ binding strength is observed, to an apparent dissociation constant of 760 nM. Such a strong dependence on ionic strength is not surprising for the reaction of a tetravalent anion with a divalent cation.

EXAMPLE IV

Photoisomerization of stilbenes

The stilbene-type indicators disclosed herein, as exemplified by stil-1 and stil-2, can exist in cis and trans isomers. Both isomers are included in the products (e.g., IX, XII, and XV) of the Wittig reactions. Separation of the isomers was attempted only with stil-1/Me and Et. Thin layer chromatography (chloroform-methanol 9:1 or 19:1 v/v) on $AgNO_3$-impregnated silica was barely able to resolve the two isomers of stil-1/Et, the cis isomer migrating more slowly. High pressure liquid chromatography on an octadecyl reverse phase column (Supelcosil LC-18 25 cm×4.6 mm, Supelco, Inc., Bellefonte, PA) and 92:8 v/v methanol-water elution also separated the isomers. In each case the cis isomer was identified by its nonfluorescence. Preparative isolation of the desired trans isomer was best accomplished by repeated recrystallization of the ester, stil-1/Me. Saponification of the pure trans ester in the dark was assumed to give pure trans penta-anion. Irradiation of the anion in aqueous solution with 365 nm light reduced both the long wavelength absorbance and the fluorescence. Assuming only the trans isomer is fluorescent (see reference 25), the photostationary state in the absence of $Ca^{2+}$ contains about 75% trans, 25% cis. This ratio of trans to cis is unusually high for a stilbene photostationary state. If crude stil-1/Me containing the original mixture of cis and trans isomers is hydrolyzed, irradiation of the anion mixture increases the absorbance and fluorescence. Photoisomerization significantly complicates the use of trans stil-1 as a fluorescent indicator. It becomes necessary to irradiate stil-1 strongly to reach photostationary equilibrium before $Ca^{2+}$ measurement begins, and even then to minimize the intensity of the excitation beam and read $Ca^{2+}$ from the ratio of excitation efficiencies at two wavelengths rather than from the absolute fluorescence intensity at any one excitation wavelength. Unfortunately, stil-1 also undergoes yet another, albeit slow, photochemical reaction in addition to cis-trans isomerism. This slow reaction causes a gradual rise in fluorescence at long (>300 nm) excitation wavelengths. It is most noticeable when a stil-1 sample is irradiated at very low $[Ca^{2+}]$, then exposed to high $Ca^{2+}$ during measurement of its excitation spectrum. A plausible but unproven explanation is the photocyclization of the non-fluorescent cis isomer to a phenanthrene (see reference 25) which could be quite fluorescent at the longer excitation wavelengths. All these complications of the stilbenes make synthesis of the disclosed indo-type and benzofuran-type dyes, in which such photochemical reactions are prevented by heterocyclic ring formation, preferable.

EXAMPLE V

Cation selectivity

Binding constants for competing cations were most thoroughly explored for fura-2. Titrations with $Mg^{2+}$ (see FIG. 6) showed dissociation constants of about 5.6 mM at 37° C. and 9.8 mM at 20° at 0.1–0.15M ionic strength. Therefore fura-2 binds $Mg^{2+}$ less strongly than does quin2, whose $Mg^{2+}$ dissociation constants are about 1 mM and 2 mM respectively at 37° and ca. 22° (see references 6 and 7). Furthermore, the effect of $Mg^{2+}$ binding on the fura-2 spectrum is quite small compared with the effect of $Ca^{2+}$, as may be seen by comparing FIG. 6 with FIG. 3. Further increases in $Mg^{2+}$ to extremely high levels (100 mM or greater) cause the excitation spectrum to go back down rather than further up. This behavior may reflect partial formation of 2 $Mg^{2+}$ − 1 dye complexes.

Binding of fura-2 to some of the physiologically more important heavy divalent metals was also briefly examined. Both stil-1 and fura-2 bind zinc with dissociation constants around 1.6–2 nM ($pK_{Zn}$ 8.6–8.8). While these values show a $Zn^{2+}:Ca^{2+}$ preference of two orders of magnitude, they are better than the values for quin2, which prefers $Zn^{2+}$ to $Ca^{2+}$ by 3.5 orders of magnitude (see reference 26). Curiously $Zn^{2+}$ shifts the fura-2 spectrum the same way that $Ca^{2+}$ does, whereas $Zn^{2+}$ quenches quin2 and therefore acts oppositely to $Ca^{2+}$. Fura-2 is also better than quin2 in rejecting $Mn^{2+}$, the $Mn^{2+}:Ca^{2+}$ preferences being 42-fold and 510-fold respectively (see reference 26). The predominant oxidation state of labile intracellular iron is +2 (see reference 27); $Fe^{2+}$ binds fura-2 between three and ten time as strongly as $Ca^{2+}$ does. A more precise estimate was prevented by experimental scatter, which may reflect more complicated stoichiometry than 1:1 or imperfectly anaerobic conditions. Both $Mn^{2+}$ and $Fe^{2+}$ quench fura-2 as expected for metals with many unpaired electrons. For comparison, EGTA prefers $Zn^{2+}$, $Mn^{2+}$, and $Fe^{2+}$ to $Ca^{2+}$, by factors of ca. 50, ca. 20, and ca. 8-fold respectively (see reference 11).

The effects on fura-2 of pH changes within the physiological range seem to be very small. FIG. 7 indicates that pH variations over a reasonable range of intracellular values hardly effect either the spectra of the $Ca^{2+}$-free or $Ca^{2+}$-bound species or the effective $Ca^{2+}$ dissociation constant.

EXAMPLE VI

Binding to membranes

Red cells were used as model membranes to test binding because they are easy to add and remove. Red cells added to a hematocrit of 17% in a solution of fura-2, fura-3, or indo-1, then centrifuged out, decreased the fluorescence of the supernatant by less than 5%. This small drop in fluorescence could have been just dilution by the small unavoidable amount of extracellular fluid added with the packed cells. Even if it were attributed entirely to binding, the amount of dye bound to a membrane would be less than that contained in a layer 0.2 microns thick of adjacent aqueous solution. Such negligible binding was found whether the medium contained 1 mM $Ca^{2+}$ or EGTA without $Ca^{2+}$.

EXAMPLE VII

Calibration equation for a dye using intensity values at two wavelengths

An important feature of the new dyes disclosed herein is the ability of $Ca^{2+}$ to change the shape and wavelength distribution of the fluorescence spectra, not just the intensity. Though quin2 also shifts its peak excitation wavelength with $Ca^{2+}$ (see FIG. 5), in practice the long-wavelength end of the excitation spectrum has too low an intensity and is too sensitive to $Mg^{2+}$. Therefore quin2 has almost always been used with excitation centered on 339 nm. Under these conditions any given fluorescence reading from intracellular quin2 has no quantitative meaning until compared with an end-of-experiment destructive calibration in which the dye is forced into two known states of high and low $Ca^{2+}$ saturation. Any intervening loss of dye or change in instrument sensitivity jeopardizes the calibration and may be mistaken for a change in $[Ca^{2+}]_i$. By contrast, if a dye shifts wavelengths upon binding $Ca^{2+}$, the ratio R of the dye's fluorescence intensities $I_1$ and $I_2$ at just two excitation wavelengths lambda$_1$ and lambda$_2$ is in principle sufficient to calculate $[Ca^{2+}]$, independent of total dye concentration, $D_T$, pathlength, or absolute sensitivity of the instrument. To this end let us define the fluorescences of completely $Ca^{2+}$-free dye at unit concentration and at excitation wavelengths lambda$_1$ and lambda$_2$ to be $F_{A1}$ and $F_{A2}$. The analogous parameters for completely $Ca^{2+}$-saturated dye are $F_{B1}$ and $F_{B2}$. For a mixture of free and $Ca^{2+}$-bound indicator at respective concentrations $D_A$ and $D_B$, the overall fluorescence intensities will be given by:

$$I_1 = D_A F_{A1} + D_B F_{B1} \quad (1a)$$

$$I_2 = D_A F_{A2} + D_B F_{B2} \quad (1b)$$

However, $D_A$ and $D_B$ are related to $[Ca^{2+}]$ by the equation for 1:1 complexation, $$D_B = D_A [Ca^{2+}]/K_d \quad (2)$$

where $K_d$ is the effective dissociation constant. The fluorescence ratio R is the ratio $$I_1/I_2 = (D_A F_{A1} + D_B F_{B1})/(D_A F_{A2} + D_B F_{B2}) = \quad (3)$$

-continued
$$(F_{A1} + F_{B1}[Ca^{2+}]/K_d)/(F_{A2} + F_{B2}[Ca^{2+}]/K_d) = R$$

Solving for $[Ca^{2+}]$ yields the calibration equation:

$$[Ca^{2+}] = K_d \cdot \left( \frac{R - (F_{A1}/F_{A2})}{(F_{B1}/F_{B2}) - R} \right) \left( \frac{F_{A2}}{F_{B2}} \right) \quad (4)$$

Note that $F_{A1}/F_{A2}$ is simply the limiting value that R can have at zero $[Ca^{2+}]$ and so may be considered $R_{min}$, while $F_{B1}/F_{B2}$ is the analogous limiting $R_{max}$ that the ratio has at saturating $[Ca^{2+}]$. The above equation may therefore be written as:

$$[Ca^{2+}] = K_d \cdot \left( \frac{R - R_{min}}{R_{max} - R} \right) \left( \frac{F_{A2}}{F_{B2}} \right) \quad (5)$$

a form closely analogous to the calibration equation for a dye using intensity values at only one wavelength:

$$[Ca^{2+}] = K_d \cdot \left( \frac{F - F_{min}}{F_{max} - F} \right) \quad (6)$$

Both equations (5) and (6) assume that the dye forms a simple 1:1 complex with $Ca^{2+}$ (equation 2), that it behaves in cells as it does in calibration media and that it is sufficiently dilute for fluorescence intensity to be linearly proportional to the concentrations of the fluorescent species (equation 1). However, equation 6 requires that F, $F_{min}$, and $F_{max}$ all be determined at the same instrumental sensitivity, optical path length, and effective total concentration of dye. These requirements are hard to satisfy when observing cells confined to a monolayer or under a microscope or in a flow cytometer, since the only really sure way to measure $F_{max}$ and $F_{min}$ requires lysing the cells and titrating the dye released. Only with disaggregated cells suspended in a cuvet can the dye concentration in the optical path be relied upon to stay unchanged despite lysis. Though methods have been proposed to calibrate without lysis, for example by using ionophore to saturate the dye with $Ca^{2+}$ then quench it with $Mn^{2+}$ (see reference 26), the evidence that ionophore does the job to completion rests on comparison with lysis. Also such methods do not compensate for dye loss due to bleaching or leakage during the main recording period. Using ratios and equation 5, dye content and instrumental sensitivity are free to change between one ratio and another since they cancel out in each ratio. Of course, stability is required within each individual ration measurement; also R, $R_{min}$, $R_{max}$ should all be measured on the same instrumentation so that any wavelength biases influence all of them equally. The data at excitation lambda$_1$ = 340 nm and lambda$_2$ = 380 nm from FIG. 3 correspond well to equation 5 within $R_{min}$ = 0.768, $R_{max}$ = 35.1, $F_{A2}/F_{B2}$ = 15.3, and $K_d$ = 135 nM. Obviously these equations are just as applicable to indo-1 emission ratios. For the data of FIG. 4 at emission lambda$_1$ = 400 nm and lambda$_2$ = 490 nm, $R_{min}$ = 0.121, $R_{max}$ = 2.60, $F_{A2}/F_{B2}$ = 2.01, and $K_d$ = 250 nM.

It should be noted that ratio operation has two main disadvantages. If tissue autofluorescence is significant, it has to be subtracted before forming the ratio, whereas it cancels out automatically in equation 6 as long as it is calcium-independent. Fortunately the brightness of the new dyes makes it easy to swamp autofluorescence. Also the instrumentation to alternate excitation wavelengths rapidly and to calculate the ratio of fluorescence intensities is not yet standardly available. In our laboratory at the University of California we have built a system in which two light sources and two monochromators are alternately selected by a butterfly-shaped sector mirror rotating at 10–30 Hz. Cancellation of large fluctuations in intensity has indeed been invaluable in studying monolayers and single small cells. However, it would be relatively difficult to provide sequential excitation wavelengths of stable relative intensity in flow cytometry, so that the emission shift of indo-1 makes it particularly attractive in this application.

TABLE 1

PROPERTIES OF NEW FLUORESCENT INDICATORS OF $Ca^{2+}$

| DYE | Apparent $K_d$ for $Ca^{2+}$ (nM) | Absorption maxima Free anion | Absorption maxima Ca complex | Emission maxima Free anion | Emission maxima Ca complex | Fluorescence quantum efficiency Free anion | Fluorescence quantum efficiency Ca complex |
|---|---|---|---|---|---|---|---|
| stil-1 | 132$^a$, 200$^b$ | 362(27) | 329(34) | 537(585) | 529(n.d.) | .14 | n.d. |
| stil-2 | 224$^c$ | 352(12) | 326(12) | 564(590) | 560(587) | .11 | .15 |
| indo-1 | 250$^b$ | 349(34) | 331(34) | 485(482) | 410(398) | .38 | .56 |
| fura-1 | 107$^b$ | 350(21) | 334(27) | 534(585) | 522(548) | .10 | .20 |
| fura-2 | 135$^a$, 224$^b$ | 362(27) | 335(33) | 512(518) | 505(510) | .23 | .49 |
| fura-3 | 140$^b$ | 370(14) | 343(25) | 564(588) | 551(599) | .13 | .21 |
| quin-2$^d$ | 80$^a$ | 354(5) | 332(5) | 492(510) | 498(525) | .03 | .14 |

$^a$In 100 mM KCl, 20° C., pH 7.1–7.2
$^b$In 115 mM KCl, 20 mM NaCl, 10 mM KMOPS, pH 7.05, 1 mM free $Mg^{2+}$, 37° C.
$^c$In 100 mM KCl, 37° C., pH 7.08
$^d$Shown here for comparison. Data taken from reference 4, p. 106.
n.d., not determined
Absorption maxima refer to the dominant peaks at longest wavelength, measured at 22 ± 2° C. in 100 mM KCl. The first number is the wavelength in nm, followed in parentheses by $10^{-3} \times$ the corresponding extinction coefficient, $M^{-1}cm^{-1}$. The data for stil-2 are for the cis-trans mixture as saponified; both the wavelengths and extinction coefficients would increase for pure trans. Extinction coefficients for fura-1 and fura-3 may be underestimated since less effort was expended on their purification than on stil-1, indo-1, and fura-2.
Emission maxima list the peak wavelengths in nm of the uncorrected and corrected (in parentheses) emission spectra. The differences between uncorrected and corrected values are greatest for stil-1 and fura-1 because they were measured on the Perkin-Elmer MPF44, whose emission characteristics are more biased than the Spex Fluorolog, on which the others were determined. Emission maxima and quantum efficiencies were measured in 100 mM KCl, 22 ± 2° C.

SUMMARY

Thus it can be seen that the present invention discloses a new class of fluorescent, indicator dyes that are specific for calcium ions. The new fluorescent, indicator dyes combine a stilbene-type fluorophore with a tetracarboxylate parent $Ca^{2+}$ chelating compound having the octacoordinate pattern of ligating groups characteristic of EGTA and BAPTA. In a first form the new dyes are composed of a BAPTA-like chelator coupled to a single fluorescent dye. In a second form the new dyes are comprised of a BAPTA-like chelator coupled to a pair of fluorescent dyes. Preferred compounds contain heterocyclic brides to reinforce the ethylenic bond of the stilbene and to reduce hydrophobicity. The new dye compounds disclosed herein are superior to existing fluorescent calcium indicators such as quin2 because the new compounds show a much stronger fluorescence, a somewhat weaker affinity for $Ca^{2+}$, a better selectivity against magnesium and heavy metals, and most importantly a wavelength shift upon $Ca^{2+}$-binding. The new dye indicators should not only supersede quin2 in many applications, but should also ease $[Ca^{2+}]_i$ measurements in adherent cells, bulk tissues, or single cells under a microscope or in a flow cytometer.

It can also be seen that the present invention discloses an improved method for synthesizing alpha-acyloxyalkyl bromides wherein the bromides wherein the bromides so synthesized are free of contaminating bis(1-bromoalkyl)ether. Such alpha-acyloxy bromides are useful to the pharmaceutical industry in the preparation of prodrugs (see references 38 and 39). The improved method is specifically exemplified herein in the synthesis of acetoxymethyl bromide, a compound useful in preparing the acetoxymethyl esters disclosed and claimed herein.

Various modifications of the invention in addition to those shown and described herein will become apparent to those skilled in the art from the foregoing description and accompanying drawings. Such modifications are intended to fall within the scope of the appended claims.

What is claimed is:

1. A chemical compound having the general formula:

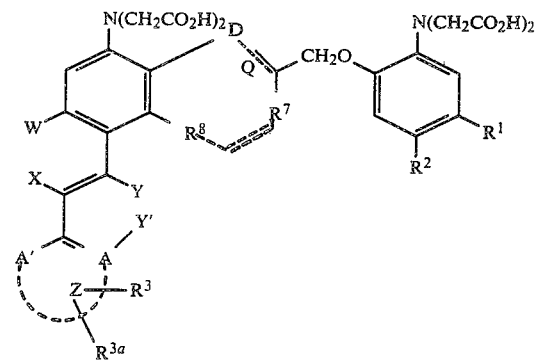

and the pharmaceutically acceptable non-toxic salts and esters thereof wherein:

$R^1$ is selected from the group comprised of —H, —$CH_3$, —F, —Cl, and —Br;

$R^2$ is selected from the group comprised of —H, —$CH_3$, —F, —Cl, —Br, and $C_0$-$C_4$ alkoxy;

$R^3$ or $R^{3a}$ are independently H or a polar, electron withdrawing function selected from the group comprised of —$CO_2H$, —$CO_2R^4$, —$CONR^5R^6$, —$SO_3H$, —$SO_2NR^5R^6$, —$SO_2CF_3$, —$COCH_3$, and —CN, or $R^3$ and $R^{3a}$ together are —(CO)$NR^5$(CO)—;

R[4] is alpha-acyloxyalkyl or a pharmaceutically acceptable esterifying group;

R[5] and R[6] are independently —H, methyl, or ethyl;

Z is an aromatic or heteroaromatic system coupled to the 5 position of one 2-aminophenoxy ring through a trans ethylenic linkage, wherein said ethylenic linkage may itself be part of an aromatic heteroaromatic ring system;

W is H and X is H; or

W and X together are O, or NR[5];

Y is H; Y' is H unless A is NR[5], O, or S; or

Y and Y' together are NR[5] and A is C;

A and A' are independently C, N, O, or S;

D is O, N, NH, or N alkyl;

Q is a double bond when D is N and a single bond otherwise; and

R[7] is H and R[8] is H or

R[7] and R[8], together with heteroatom D, the carbon adjacent R[7], and the phenyl ring adjacent to R[8], form a quinoline ring system D is N and Q is a double bond.

2. The compound of claim 1 wherein said tetraacetic acid esters include alpha-acyloxyalkyl ester groups.

3. The compound of claim 2, wherein said alpha-acyloxyalkyl ester groups are acetoxymethyl ester groups.

4. The compound of claim 1 wherein Z is a benzene ring and W, X, Y and Y' are —H.

5. The compound of claim 1 wherein W and X together are oxygen, and together with the ethylenic bridge and one 2-aminophenoxy ring constitute a substituted benzofuran.

6. The compound of claim 1 wherein A is carbon and Y and Y' together are nitrogen, and together with the ethylenic bridge and ring Z constitute a substituted indole.

7. A bis(2-aminophenoxy)ethane-N,N,N',N'-tetraacetic acid having the general formula:

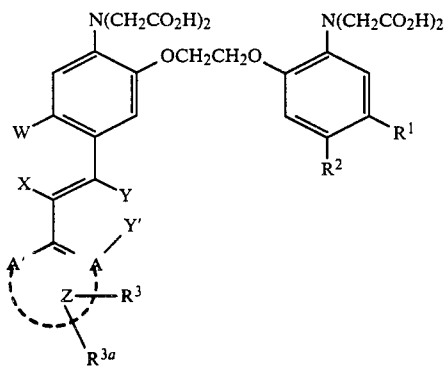

and the pharmaceutically acceptable non-toxic salts and esters thereof wherein:

R[1] is selected from the group comprised of —H, —CH$_3$, —F, —Cl, and —Br;

R[2] is selected from the group comprised of —H, —CH$_3$, —F, —Cl, —Br, and C$_0$-C$_4$ alkoxy;

R[3] or R[3a] are independently H or a polar, electron withdrawing function selected from the group comprised of —CO$_2$H, —CO$_2$R[4], —CONR[5]R[6], —SO$_3$H, —SO$_2$NR[5]R[6], —SO$_2$CF$_3$, —COCH$_3$, and —CN, or R[3] and R[3a] together are —(CO)NR[5](CO)—;

R[4] is alpha-acyloxyalkyl or a pharmaceutically acceptable esterifying group;

R[5] and R[6] are independently —H, methyl, or ethyl;

Z is an aromatic or heteroaromatic system coupled to the 5 position of one 2-aminophenoxy ring through a trans ethylenic linkage, wherein said ethylenic linkage may itself be part of an aromatic heteroaromatic ring system;

W is H and X is H; or

W and X together are O, or NR[5];

Y is H; Y' is H unless A is NR[5], O, or S; or

Y and Y' together are NR[5] and A is C; and

A and A' are independently C, N, O or S.

8. The compound of claim 7 wherein said tetraacetic acid esters include alpha-acyloxyalkyl esters.

9. The compound of claim 8, wherein said alpha-acyloxyalkyl ester groups are acetoxymethyl ester groups.

10. The compound of claim 7 wherein Z is a benzene ring and W, X, Y and Y' are —H.

11. The compound of claim 7 wherein W and X together are oxygen, and together with the ethylenic bridge and one 2-aminophenoxy ring constitute a substituted benzofuran.

12. The compound of claim 7 wherein A is carbon and Y and Y' together are nitrogen, and together with the ethylenic bridge and ring Z constitute a substituted indole.

13. A chemical compound having the general formula:

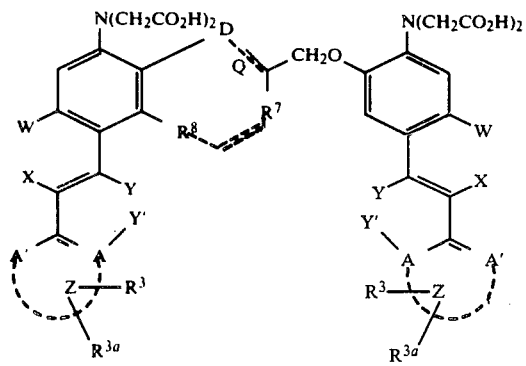

and the pharmaceutically acceptable non-toxic salts and esters thereof wherein:

R[3] or R[3a] are independently H of a polar, electron withdrawing function selected from the group comprised of —CO$_2$H, —CO$_2$R[4], —CONR[5]R[6], —SO$_3$H, —SO$_2$NR[5]R[6], —SO$_2$CF$_3$, —COCH$_3$, and —CN, or R[3] and R[3a] together are —(CO)NR[5](CO)—;

R[4] is alpha-acyloxyalkyl or a pharmaceutically acceptable esterifying group;

R[5] and R[6] are independently —H, methyl, or ethyl;

Z is an aromatic or heteroraromatic system coupled to the 5 position of one 2-aminophenoxy ring through a trans ethylenic linkage, wherein said ethylenic linkage may itself be part of an aromatic heteroaromatic ring system;

W is H and X is H; or

W and X together are O, or NR[5];

Y is H; Y' is H unless A is NR[5], O, or S; or

Y and Y' together are NR[5] and A is C;

A and A' are independently C, N, O, or S;

D is O, N, NH, or N alkyl;

Q is a double bond when D is N and a single bond otherwise; and

R[7] is H and R[8] is H or

R[7] and R[8], together with heteroatom D, the carbon adjacent R[7], and the phenyl ring adjacent to R[8], form a quinoline ring system D is N and Q is a double bond.

14. The compound of claim 13 wherein said tetraacetic acid esters include alpha-acyloxyalkyl esters.

15. The compound of claim 14, wherein said alpha-acyloxyalkyl ester groups are acetoxymethyl ester groups.

16. The compound of claim 13 wherein Z is a benzene ring and W, X, Y and Y' are —H.

17. The compound of claim 13 wherein W and X together are oxygen, and together with the ethylenic bridge and one 2-aminophenoxy ring constitute a substituted benzofuran.

18. The compound of claim 13 wherein A is carbon and Y and Y' together are nitrogen, and together with the ethylenic bridge and ring Z constitute a substituted indole.

19. A bis(2-aminophenoxy)ethane-N,N,N', N'-tetraacetic acid having the general formula:

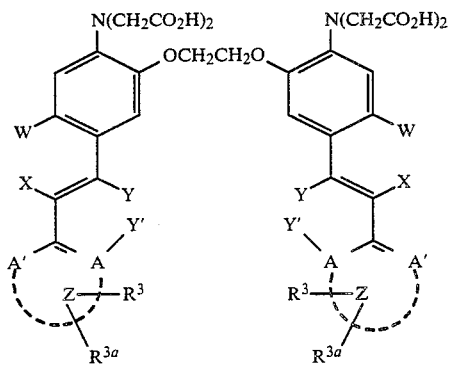

and the pharmaceutically acceptable non-toxic salts and esters thereof wherein:

R[3] or R[3a] are independently H or a polar, electron withdrawing function selected from the group comprised of —CO$_2$H, —CO$_2$R[4], —CONR[5]R[6], —SO$_3$H, —SO$_2$NR[5]R[6], —SO$_2$CF$_3$, —COCH$_3$, and —CN, or R[3] and R[3a] together are —(CO)NR[5](CO)—;

R[4] is alpha-acyloxyalkyl or a pharmaceutically acceptable esterifying group;

R[5] and R[6] are independently —H, methyl, or ethyl;

Z is an aromatic or heteroaromatic system coupled to the 5 position of one 2-aminophenoxy ring through a trans ethylenic linkage, wherein said ethylenic linkage may itself be part of an aromatic heteroaromatic ring system;

W is H and X is H; or

W and X together are O, or NR[5];

Y is H; Y' is H unless A is NR[5], O, or S; or

Y and Y' together are NR[5] and A is C; and

A and A' are independently C, N, O, or S.

20. The compound of claim 19 wherein said tetraacetic acid esters include alpha-acyloxyalkyl esters.

21. The compound of claim 20, wherein said alpha-acyloxyalkyl ester groups are acetoxymethyl esters.

22. The compound of claim 19 wherein Z is a benzene ring and W, X, Y and Y' are —H.

23. The compound of claim 19 wherein W and X together are oxygen, and together with the ethylenic bridge and one 2-aminophenoxy ring constitute a substituted benzofuran.

24. The compound of claim 19 wherein A is carbon and Y and Y' together are nitrogen, and together with the ethylenic bridge and ring Z constitute a substituted indole.

25. A fluorescent, calcium binding compound comprised of 1-(2-amino-5-[(2-(4-carboxyphenyl)-E-ethenyl-1-]phenoxy)-2-(2'-amino-5'-methylphenoxy) ethane-N,N,N',N'-tetraacetic acid and the pharmaceutically acceptable non-toxic salts and esters thereof 26. A fluorescent, calcium binding compound comprised of 1-(2-amino-5-[(2-(4-N,N-dimethylsulfonamidophenyl)-E-ethenyl-1-]phenoxy), 2-(2'-amino-5'-methylphenoxy)ethane-N,N,N',N'-tetraacetic acid and the pharmaceutically acceptable non-toxic salts and esters thereof.

27. A fluorescent, calcium binding compound comprised of 1-(2-amino-5-[6-carboxyindolyl-2]-phenoxy)-2-(2'-amino-5'-methylphenoxy)ethane-N, N,N',N'-tetraacetic acid and the pharmaceutically acceptable non-toxic salts and esters thereof.

28. A fluorescent, calcium binding compound comprised of 1-(2-(4-carboxyphenyl)-6-amino benzofuranoxy-5-)-2-(2'-amino-5'-methylphenoxy)ethane-N, N,N',N'-tetraacetic acid and the pharmaceutically acceptable non-toxic salts and esters thereof.

29. A fluorescent, calcium binding compound comprised of 1-(2-(4-cyanophenyl)-6-aminobenzofuranoxy-5-)-2-(2'-amino-5'-methylphenoxy)ethane-N, N,N',N'-tetraacetic acid and the pharmaceutically acceptable non-toxic salts and esters thereof.

30. A fluorescent, calcium binding compound comprised of 1-(2-(5'-carboxyoxazol-2'-yl)-6-aminobenzofuranoxy-5-)-2-(2'-amino-5'-methylphenoxy-ethane-N, N,N',N'-tetraacetic acid and the pharmaceutically acceptable non-toxic salts and esters thereof.

* * * * *